US010675012B2

(12) United States Patent
Larsen et al.

(10) Patent No.: US 10,675,012 B2
(45) Date of Patent: Jun. 9, 2020

(54) JOINT ASSEMBLY FOR MEDICAL DEVICES

(71) Applicant: W.L. Gore & Associates, Inc., Newark, DE (US)

(72) Inventors: Coby C Larsen, Flagstaff, AZ (US); Steven J Masters, Flagstaff, AZ (US); Thomas R McDaniel, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 917 days.

(21) Appl. No.: 13/834,562

(22) Filed: Mar. 15, 2013

(65) Prior Publication Data

US 2014/0142617 A1 May 22, 2014

Related U.S. Application Data

(60) Provisional application No. 61/727,328, filed on Nov. 16, 2012.

(51) Int. Cl.
*A61B 17/00* (2006.01)
*A61B 17/12* (2006.01)
*A61F 2/01* (2006.01)

(52) U.S. Cl.
CPC .... *A61B 17/0057* (2013.01); *A61B 17/12031* (2013.01); *A61B 17/12122* (2013.01);
(Continued)

(58) Field of Classification Search
CPC .......... A61B 17/12; A61B 2017/12004; A61B 17/12022; A61B 17/12131; A61B 17/1214; A61B 17/12145; A61B 17/12168; A61B 17/12172; A61B 17/12031; A61B 17/12036; A61B 17/12027;
(Continued)

(56) References Cited

U.S. PATENT DOCUMENTS 3,874,388 A 4/1975 King
4,762,129 A 8/1988 Bonzel
(Continued)

FOREIGN PATENT DOCUMENTS

EP 2478868 A1 7/2012
WO W01996032882 A1 10/1996
WO W02008041225 A2 1/2008

OTHER PUBLICATIONS

International Search Report and Written Opinion for PCT/US2013/070371, dated May 16, 2014, 29 pages.
(Continued)

*Primary Examiner* — Victoria J Hicks

(57) ABSTRACT

A device for occluding an aperture in a body of a patient includes a frame that includes a plurality of elongate members and a hub component that includes a plurality of attachment members, wherein for each elongate member of the plurality of elongate members a first end of the elongate member is fixedly attached to an attachment member of the plurality of attachment members at an attachment region. The frame and the hub component together form at least one occlusive element. Each receptacle of the plurality of attachment members is configured to pivot with respect to the hub component, such that each attachment region is movable with respect to the hub component.

22 Claims, 15 Drawing Sheets

(52) U.S. Cl.
CPC .. *A61B 17/12172* (2013.01); *A61B 17/12177* (2013.01); *A61F 2/01* (2013.01); *A61B 17/12036* (2013.01); *A61B 17/12109* (2013.01); *A61B 2017/00243* (2013.01); *A61B 2017/00477* (2013.01); *A61B 2017/00575* (2013.01); *A61B 2017/00579* (2013.01); *A61B 2017/00592* (2013.01); *A61B 2017/00597* (2013.01); *A61B 2017/00601* (2013.01); *A61B 2017/00619* (2013.01); *A61B 2017/00623* (2013.01); *A61B 2017/00632* (2013.01); *A61B 2017/00641* (2013.01); *A61B 2017/00884* (2013.01); *A61B 2017/00893* (2013.01); *A61B 2017/00902* (2013.01); *A61B 2017/1205* (2013.01); *A61B 2017/12095* (2013.01); *A61F 2002/011* (2013.01)

(58) Field of Classification Search
CPC .......... A61B 17/12122; A61B 17/0057; A61B 17/12177; A61F 2/01; A61F 2002/016; A61F 2/00
USPC ....... 606/191, 192, 193, 194, 213, 221, 151, 606/157, 158, 1, 200; 128/831, 833, 834, 128/835, 836, 837, 838, 839, 840, 841, 128/887; 609/119; 604/107, 115, 105; 600/102
See application file for complete search history.

(56) References Cited

U.S. PATENT DOCUMENTS

| | | |
|---|---|---|
| 5,040,548 A | 8/1991 | Yock |
| 5,061,273 A | 10/1991 | Yock |
| 5,486,193 A | 1/1996 | Bourne et al. |
| 5,626,599 A | 5/1997 | Bourne et al. |
| 6,080,182 A | 6/2000 | Shaw et al. |
| 6,165,197 A | 12/2000 | Yock |
| 6,488,706 B1 | 12/2002 | Solymar |
| 6,589,265 B1 | 7/2003 | Palmer |
| D493,223 S | 7/2004 | Solymar |
| 8,801,746 B1 * | 8/2014 | Kreidler .................... A61F 2/01 606/200 |
| 2003/0023265 A1 | 1/2003 | Forber |
| 2003/0149463 A1 | 8/2003 | Solymar et al. |
| 2006/0122646 A1 | 6/2006 | Corcoran |
| 2006/0241687 A1 | 10/2006 | Glaser et al. |
| 2007/0118176 A1 | 5/2007 | Opolski et al. |
| 2008/0033475 A1 | 2/2008 | Meng |
| 2009/0012559 A1 | 1/2009 | Chanduszko |
| 2009/0099647 A1 * | 4/2009 | Glimsdale .......... A61B 17/0057 623/1.35 |
| 2010/0057195 A1 | 3/2010 | Roeder |
| 2011/0112547 A1 | 5/2011 | Uihlein et al. |
| 2012/0078295 A1 | 3/2012 | Steiner |
| 2012/0143242 A1 | 6/2012 | Masters |
| 2012/0165919 A1 | 6/2012 | Cox et al. |
| 2012/0283768 A1 | 11/2012 | Cox et al. |
| 2013/0073029 A1 | 3/2013 | Shaw |
| 2013/0138138 A1 | 5/2013 | Clark et al. |
| 2014/0018841 A1 | 1/2014 | Peiffer et al. |
| 2014/0142610 A1 | 5/2014 | Larsen |
| 2014/0364941 A1 * | 12/2014 | Edmiston ......... A61B 17/12022 623/2.11 |

OTHER PUBLICATIONS

Invitation to Pay Additional Fees and Partial International Search for PCT/US2013/070371, 5 pages, 2014.
International Search Report and Written Opinion for PCT/US2013/067510, dated Feb. 13, 2014, 12 pages.

* cited by examiner

JOINT ASSEMBLY FOR MEDICAL DEVICES

CROSS-REFERENCE TO RELATED APPLICATIONS

This application claims priority to U.S. Provisional Application No. 61/727,328, filed Nov. 16, 2012. The disclosure of the prior application is considered part of and is incorporated by reference in the disclosure of this application.

TECHNICAL FIELD

The present disclosure relates to joint assemblies that may be used with medical devices, including implantable devices that can be used to occlude apertures, conduits, or structures within a patient.

BACKGROUND

Cardiac features such as septal defects and atrial appendages often contribute to cardiac blood flow disturbance, which is associated with a number of cardiac-related pathologies. For example, complications caused by blood flow disturbance within the left atrial appendage (LAA) and associated with atrial fibrillation can be a contributor to embolic stroke. The LAA is a muscular pouch extending from the anterolateral wall of the left atrium of the heart and serves as a reservoir for the left atrium. During a normal cardiac cycle, the LAA contracts with the left atrium to pump blood from the LAA, and generally prevents blood from stagnating within the LAA. However, during cardiac cycles characterized by arrhythmias (e.g., atrial fibrillation), the LAA often fails to sufficiently contract, which can allow blood to stagnate within the LAA. Stagnant blood within the LAA is susceptible to coagulating and forming a thrombus, which can dislodge from the LAA and ultimately result in an embolic stroke or other thromboembolic complication.

In some instances, thrombus formation in the LAA of arrhythmic patients can be minimized by occluding the LAA. Some LAA occlusion devices that are placed within the LAA or across the ostium of the LAA (the opening between the left atrium and the LAA) terminate at an elongate eyelet at each end of the device. The elongate eyelet of the device that faces the left atrium after implantation can often protrude from the device into the left atrial chamber, which can disturb blood flow within the left atrial chamber and can lead to thrombus formation and accumulation near the eyelet. Furthermore, a protruding eyelet may present a blood-material interface that is different than that which exists along other atrial-facing regions of the occluder device. Thrombus formation may increase the risk of stroke, and serious injury or death can result if the thrombus becomes dislodged and enters the circulatory system.

SUMMARY

In some aspects, a device for occluding an aperture within a body of a patient includes a frame comprising a plurality of elongate members, and a hub component comprising a plurality of attachment members. A first end of each elongate member of the plurality of elongate members is fixedly attached to an attachment member of the plurality of attachment members at an attachment region. The frame and the hub component together form at least one occlusive element. Each attachment member of the plurality of attachment members is configured to pivot with respect to the hub component, such that each attachment region is movable with respect to the hub component.

In some implementations, each attachment region may be movable with multiple degrees of freedom with respect to the hub component. Each attachment region may be movable with one degree of freedom with respect to the hub component. The hub component may include a plurality of sockets, each attachment member of the plurality of attachment members may include a generally spherical member and each of the generally spherical members may be received by a socket of the plurality of sockets to form a ball-and-socket arrangement. Each socket of the plurality of sockets may include one or more positional stops adapted to maintain a position of the received generally spherical member. A tension on the generally spherical member may increase as the generally spherical member pivots within the socket. Each elongate member of the plurality of elongate members may be formed from a single wire. The occlusive element may include a substantially planar face. The hub component may be a first hub component disposed at a proximal end of the device, and the device may include a second hub component disposed at a distal end of the device. The frame of the device may include a covering that covers at least a portion of the frame, and the covering may cover at least a portion of the hub. The covering may include a membrane. The membrane may include a fluoropolymer including PTFE such as ePTFE, and may include a copolymer. The plurality of attachment members may be substantially equally spaced about the hub component. The hub component may be disposed substantially at a center of the occlusive element. Each elongate member of the plurality of elongate members may move, at the respective attachment region, independently of other elongate members of the plurality of elongate members. The plurality of elongate members may have an elastic property and a preformed shape, and the frame may collapse to assume a delivery configuration and may expand to the preformed shape to assume a deployed configuration. At least one elongate member of the plurality of elongate members may move parallel to a center axis of the hub component. The hub component may define an aperture that passes through the hub component along a center axis of the hub component. The hub component may include a plurality of sockets, and each attachment member of the plurality of attachment members may be coupled to a socket via one or more pins. The attachment members may comprise receptacles for connection of the elongate member to the hub. The attachment member may be integral with the first end of the elongate member. The occlusive element may include a substantially convex face. The occlusive element may include a substantially concave face. The device may include at least one fixation member that extends from at least one of the elongate members.

In some aspects, a method of occluding an aperture within a body of a patient includes delivering a device to the aperture and deploying the device such that device forms an occlusive element. The device is configured to occlude the aperture. The occlusive element includes a portion of a frame including a plurality of elongate members, and a hub component including a plurality of attachment members. A first end of each elongate member of the plurality of elongate members is fixedly attached to a receptacle of the plurality of attachment members at an attachment region. Each attachment member of the plurality of attachment members is configured to pivot with respect to the hub component, such that each attachment region is movable with respect to the hub component.

In some implementations, the method may include loading the device on a catheter and passing the device and the catheter through a delivery sheath. The frame may collapse as the device is passed through the delivery sheath. Deploying the device may include advancing the device through the delivery sheath, such that at least a portion of the device exits the delivery sheath distal of the delivery sheath. The frame may expand as the device exits the delivery sheath. Deploying the device may include pulling the delivery sheath away from the aperture while maintaining a position of the device. The plurality of attachment members may be locked into respective positions as the device is deployed. The aperture may be located within a vessel, and deploying the device may substantially close the vessel. The aperture may be located within a heart.

The details of one or more embodiments are set forth in the accompanying drawings and the description below. Other features, objects, and advantages will be apparent from the description and drawings, and from the claims.

BRIEF DESCRIPTION OF THE DRAWINGS

Like reference symbols in the various drawings indicate like elements.

DETAILED DESCRIPTION

This document provides joint assemblies for use with medical devices, including but not limited to implantable medical devices that can be used to occlude apertures, holes, defects, appendages, conduits, cavities, vessels, organs, or structures within a patient. In some embodiments, the joint assemblies provided herein include receptacles to couple a plurality of elongate frame members to a hub component. Each receptacle of the plurality of elongate frame members is configured to pivot with respect to the hub component, such that each elongate frame member attachment region is movable with respect to the hub component.

Figure 1:
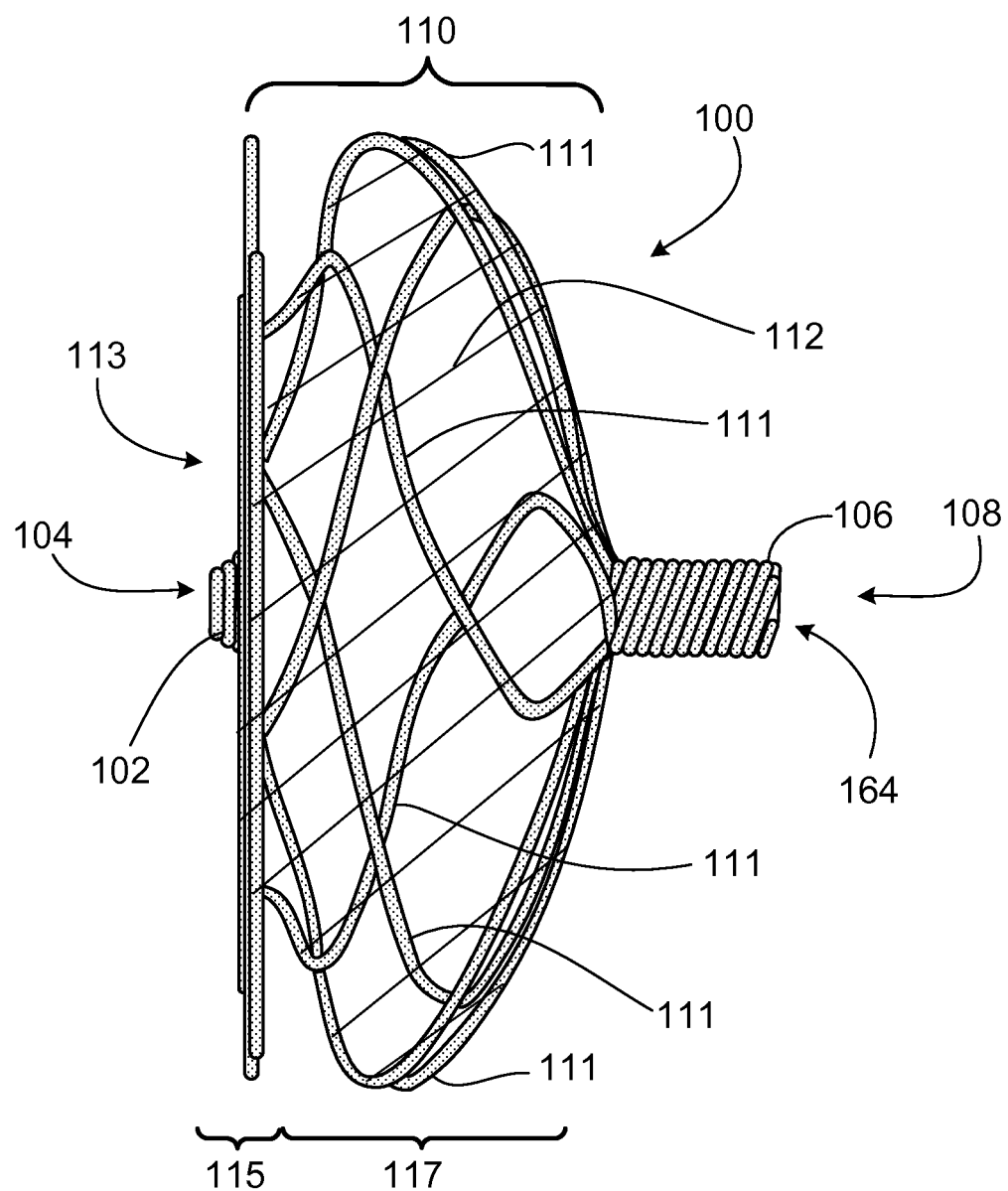
FIG. 1 is a side view of an example occlusion device that can be used to occlude a hole, defect, aperture, or appendage within a body of a patient.

FIG. 1 illustrates an example occlusion device 100 that can be used to occlude a hole, defect, aperture, appendage, vessel or conduit within a body of a patient. In some examples, the occlusion device 100 can be used to occlude a left atrial appendage (LAA) of a human heart. The occlusion device 100 can be delivered in an endovascular manner through or over a catheter system to a delivery site, such as the LAA or other appropriate delivery site. In this manner, the occlusion device 100 can be deployed within the LAA or across the ostium of the LAA to isolate the LAA from the main chamber of the left atrium (left atrial chamber), for example. This may prevent thrombus formation within the LAA and/or thrombus exit from the LAA, as will be described in more detail below. The occlusion device 100 includes a hub 102 near a proximal end 104 of the occlusion device 100, an eyelet 106 near a distal end 108 of the occlusion device, and a frame 110, comprised of elongate members 111, that extends between the hub 102 and the eyelet 106. The occlusion device 100 further includes a covering 112 (represented schematically in FIG. 1) that covers at least a portion of the frame 110. In some embodiments, the covering 112 may cover the entire frame 110. In some embodiments, the covering 112 may cover all or a portion of the hub 102. In some embodiments, the occlusion device 100 may include a second hub 102 (not shown) that may replace the eyelet 106 near the distal end 108 of the device 100. In some embodiments, medical devices may include more than two hubs or eyelets, each of which could utilize the joint assemblies provided herein.

As shown in FIG. 1, a proximal-facing portion of the occlusion device 100 includes a substantially planar face 113 comprising the hub 102 and portions of the elongate members 111. When deployed to occlude the LAA of a patient, for example, the substantially planar face 113 may be oriented toward the left atrial chamber and may not substantially protrude into the left atrial chamber. In particular, the hub 102, or a proximal-facing surface of the hub 102, may be generally co-planar with the portions of the elongate members that form the substantially planar face 113 of the occlusion device 100, in some examples. The elongate members 111 may exit the hub 102, and may do so within a particular plane, where the hub 102 is also substantially within the particular plane. Also, the hub 102 may not substantially protrude into the left atrial chamber when the occlusion device 100 is deployed to occlude the LAA. In this manner, the occlusion device 100 may minimize disturbance of blood flow within the left atrial chamber and may minimize or reduce risk of thrombus formation on or near the proximal-facing portion 104 of the occlusion device 100, for example. While the example occlusion device 100 includes substantially planar faces, some medical device embodiments that can also utilize the joint assemblies provided herein do not have such substantially planar faces.

In other examples, the hub 102 may be recessed in the distal direction from a plane formed by the portions of the elongate members 111. For example, the portions of the elongate members 111 may be oriented proximally in comparison to the hub 102, such that the portions of the elongate members 111 and the hub 102 form a plane with a concave or recessed area in which the hub 102 is disposed. In some examples, the portions of the elongate members 111 may be oriented distally in comparison to the hub 102, such that the portions of the elongate members 111 and the hub 102 form a plane with a convex area in which the hub 102 is disposed.

In some implementations, the occlusion device 100 may assume two or more configurations. In some embodiments, each of the two or more configurations is distinct from the others of the two or more configurations. For example, the occlusion device 100 may assume a delivery configuration when the occlusion device 100 is delivered over or through a catheter to a delivery site (refer to FIG. 5), and may assume a deployed configuration following deployment from the catheter at the delivery site (refer to FIG. 6). In the example shown in FIG. 1, the occlusion device 100 is generally shown in a deployed configuration. In the deployed configuration, the occlusion device 100 includes an occlusion member 115, generally having the shape of a disc in this example, that can occlude an aperture at a delivery site, and a support member 117 that can provide support to the occlusion device 100. For example, the occlusion member 115 can isolate the LAA from the left atrial chamber, in some implementations. In this example, the occlusion member 115 includes the hub 102, proximal portions of the elongate members 111, and a proximal portion of the covering 112. The support member 117 includes distal portions of the elongate members 111, a distal portion of the covering 112, and in some embodiments can include one or more securing members (not shown in FIG. 1, refer to FIG. 4) that can secure the frame 110 to tissue at the delivery site. In some implementations, the covering 112 covers the portion of the frame 110 that forms the occlusion member 115, but does not cover the portion of the frame that forms the support member 117. Other configurations may include partially deployed configurations, which the occlusion device 100 may assume as the device is being deployed from the catheter system, for example.

In various embodiments, the occlusion member 115 may be shaped appropriately to occlude an aperture. In certain instances, the plurality of elongate members 111 each form a curvature tapering the frame 110 to a distal end portion 108 of the frame to reduce a diameter of the frame 110 ending the curvature at the distal end portion 108. In some examples, the occlusion member 115 may be shaped to partially occlude an aperture. The occlusion member 115 may have, from a frontal view of the proximal portion 104 of the device 100, a shape of a circle, an oval, a square, a rectangle, a triangle, a diamond, a semi-circle, a crescent, or any other appropriate shape to occlude a particular opening or aperture. In some embodiments, the hub 102 may be positioned generally centrally with respect to a proximal face 113 of the occlusion member 115. For example, if the proximal face 113 of the occlusion member 115 is shaped as a circle, the hub 102 may be positioned generally near a center of the circle. Similarly, if the proximal face of the occlusion member 115 is shaped as a square, the hub 102 may be positioned generally near a center of the square, or near the center of an oval or rectangle for devices with occlusion members 115 having these shapes. In some embodiments, the hub 102 may be positioned non-centrally with respect to a proximal face 113 of the occlusion member 115. For example, if the proximal face 113 of the occlusion member 115 is shaped as a semi-circle, the hub 102 may be positioned generally near a midpoint of a straight (e.g., diameter-defining) edge of the semi-circle.

Figure 2:
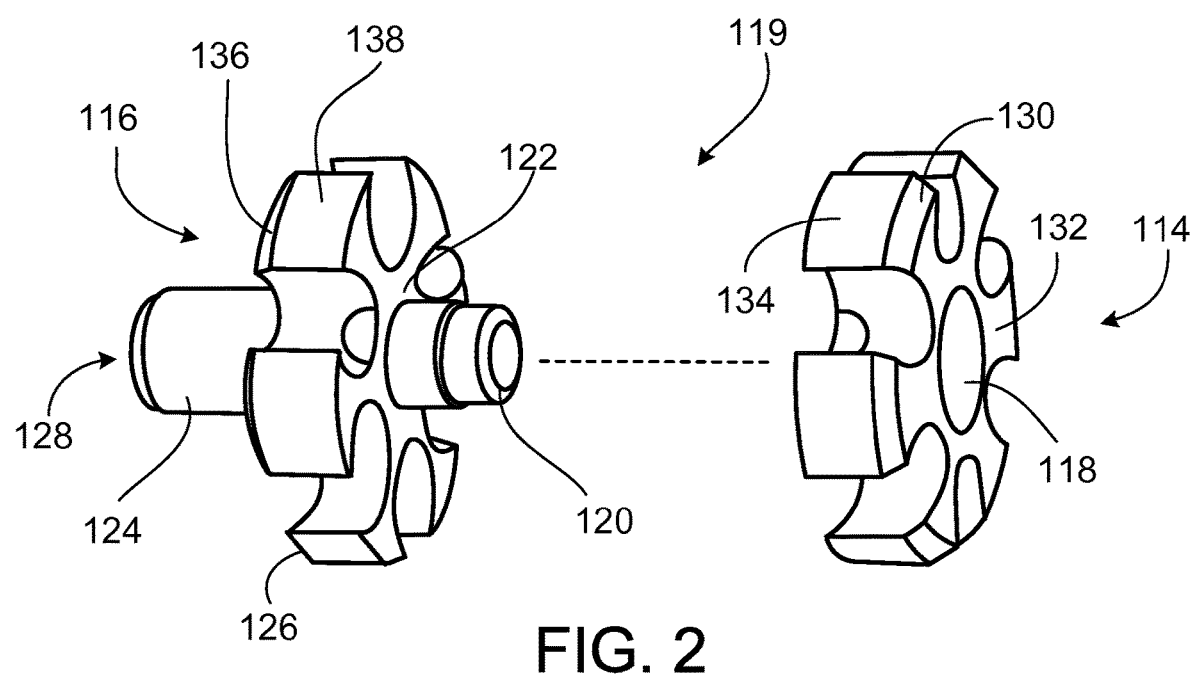
FIG. 2 is an exploded view of an example hub, which may correspond to the hub of the occlusion device of FIG. 1.

FIG. 2 is an exploded view of an example hub 119, which may correspond to hub 102 of the occlusion device 100 of FIG. 1 in some implementations. While in some implementations the body of the example hub 119 includes two pieces, in other implementations a single-piece hub body or a hub having a body with three or more pieces may be used. Referring to FIG. 2, the example hub 119 includes a first hub base member 114 and a second hub base member 116, formed to engage or to contact one another. The first hub base member 114 includes a central hole 118 that is sized to receive a central, elongate projection 120 that extends from a distal surface 122 of the second hub base member 116. In some implementations, laser billet welds may be used to attach the first and second hub base members 114, 116, to the elongate projection 120 and thereby engage the first and second hub base members 114, 116. The male and female mating features may also attach by a press fit or snap fit, or may be attached with an adhesive bond, or a bond formed by other bonding methods. In some examples, combinations of the foregoing may be used (e.g., adhesive and press fit). A tubular projection 124 extends from a proximal surface 126 of the second hub base member 116 and defines a hole 128 that is sized to engage a distal end of a delivery catheter, as will be discussed in more detail below. In some embodiments, the hole 128 may be a threaded hole or a keyed hole. In some implementations, the first hub base member 114 has a beveled edge 130 at an intersection of a distal surface 132 and a sidewall 134 of the first hub base member 114. Similarly, in some implementations the second hub base member 116 has a beveled edge 136 at an intersection of the proximal surface 126 and a sidewall 138 of the second hub base member 116. The beveled edges 130, 136 can allow for lower delivery or retrieval forces when delivering or retrieving device 100, for example.

As assembled (see FIG. 3A), in some examples the hub 119 may have a diameter of about 1.2 mm to about 1.9 mm and may have a thickness (as measured between the proximal surface 126 and distal surface 132) of about 0.75 mm to about 1.53 mm. (As defined herein, the term "about" refers to a value falling within a range encompassed by +/−5% or +/−10% of a given value.) In other embodiments, the hub 119 may be provided with a different diameter to accommodate, for example, mating of the hub 119 with a particular delivery catheter. Hub thickness may similarly be varied depending on the particular implementation. In an alternative embodiment, hub 119 may be formed as a single component (as will be discussed in more detail below).

Figure 3A:
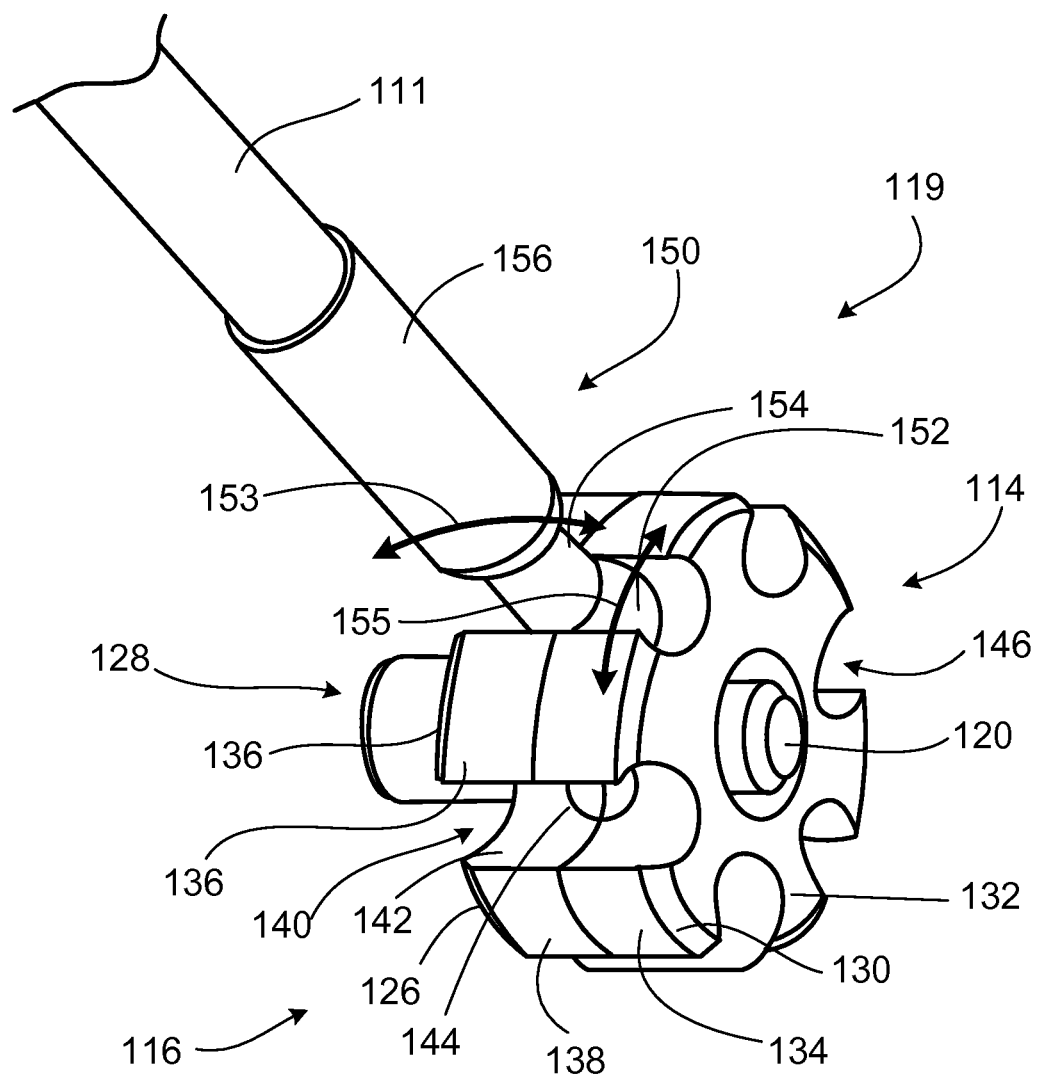
FIG. 3A is a perspective view of the hub of FIG. 2, as assembled with a portion of a frame of the occlusion device of FIG. 1.

FIG. 3A is a perspective view of the hub 119 of FIG. 2, assembled with a portion of the frame of the occlusion device 100 of FIG. 1. Six sockets 140 are shown in FIG. 3A, and each of the sockets 140 includes a socket opening 146 defined by the sidewalls 134, 138 of the hub 119. In this example, the sockets 140 are spaced substantially equidistantly around the hub 119 and extend at an angle of about 90° from the sidewalls 134, 138 of the hub 119. In some examples, the sockets 140 may be spaced about 0.12 mm to about 0.25 mm from one another (as measured from an edge of one socket 140 to a nearest edge of an adjacent socket 140), and the openings 146 of the sockets 140 may have a width of about 0.20 mm to about 0.40 mm.

In some embodiments, the interior region of each socket 140 includes a generally semi-spherical pocket 144. The generally semi-spherical pockets 144 are formed when the first and second hub base members 114, 116 are engaged. Each socket 140 further includes two semi-cylindrical channels 142 extending from opposite sides of each semi-spherical pocket 144. When assembled with receptacles 150 as will be described below, each of the semi-spherical pockets 144 constrains in at least a first dimension a generally spherical member 152 of a receptacle 150. The channels 142 and the pockets 144 may have radii of about 0.35 mm to about 0.65 mm and about 0.12 mm to about 0.51 mm, respectively. In some embodiments, a hub may include fewer than six sockets (e.g., two, three, four, five), or more than six sockets (e.g., seven, eight, nine, ten, twelve, or more).

In this example, each receptacle 150 includes a generally spherical member 152 attached to a neck region 154 that is further attached to a tubular member 156 that is sized to receive and surround a respective end portion of an elongate member 111. For simplicity, only a single receptacle 150 and a single elongate member 111 is shown in FIG. 3A, but when fully assembled the device may include a number of receptacles 150 and elongate members 111 equal to the number of sockets 140 (six, in this example) of the hub 119. Regarding the receptacles 150, the neck region 154 may have a first diameter, and the tubular member 156 may have a second diameter that is larger than the diameter of the neck region 154. Furthermore, a diameter of the spherical member 152 may be larger than the diameter of the neck region 154.

The elongate members 111 may be attached to the receptacles 150 in various manners. For example, an end of each elongate member 111 may be placed within a tubular member 156 of a receptacle 150 and laser welded therein (e.g., with a circumferential, 360 degree laser weld). Other examples of ways the elongate members 111 may be attached to the tubular members 156 of the receptacles 150 can include a mechanical crimp of the tubular member 156 around the elongate member 111 (e.g., a micro-swedge joint), an adhesive connection, an RF weld, or an ultrasonic bond, or combinations of the techniques. In various implementations, the ends of the elongate members may be inserted about 0.60 mm to about 2.0 mm into the tubular members 156. In some examples, the elongate members 111 are inserted into the elongate tubular members 156 of the receptacles 150 to a depth that is about three times the diameter of the elongate members 111.

As described above, a first end of an elongate member 111 can be fixedly attached to a receptacle 150 at an attachment region. The receptacle 150 is configured to pivot with respect to the hub 102, such that the attachment region is movable with respect to the hub 102. The elongate members 111 are securely joined with tubular members 156 such that collective positions of the receptacles 150 affect the overall shape of the frame 110. Termination of the elongate members 111 within the receptacles 150 allows the proximal end 104 of the occlusion device 100 to form the substantially planar face 113 when all of the receptacles 150 extend substantially parallel to the proximal surface 126 of the hub base member 116.

The spherical members 152 can be sized to be received into the semi-spherical pockets 144 of the sockets 140 while allowing clearance between the spherical members 152 and the socket openings 146 such that the spherical members 152 can pivot within the sockets 140. The spherical members 152 may be permitted to pivot within the sockets 140 with one degree of freedom (as indicated by a first arrow 153). In some embodiments, a clearance region between outer surfaces of the spherical members 152 and inner surfaces of the semi-spherical pockets 144 may allow the spherical members 152 to minimally pivot with a second degree of freedom (as indicated by a second arrow 155). Each receptacle 150 (and the attached end of the associated elongate member 111) may generally pivot independently of the other receptacles 150 (and elongate members 111). The side walls 134, 136 of the hub 119 may generally constrain movement of the receptacle 150 in the direction indicated by the first arrow 153. In some embodiments, the clearance between the spherical members 152 and the semi-spherical pockets 144 is such that stresses exerted on the spherical members 152 may increase as the receptacles 150 pivot within the sockets 140. As the spherical members 152 pivot within the semi-spherical pockets 144, the spherical members 152 may receive varying tensile and compressive forces that depend on the shapes that the elongate members 111 take at the delivery site. As the occlusion device 100 is collapsed and moved through a catheter sheath (as will be discussed in more detail below), the spherical members 152 may experience more tensile forces than compressive forces within the semi-spherical pockets 144. In some implementations, the first hub base member 114 and the second hub base member 116 may be press fit onto the spherical members 152 of the receptacles 150. In some implementations, the spherical members 152 may be snap fitted into the sockets 140 of the hub 102 or the hub assembly 119. The spherical members 152 may have a diameter of about 0.35 mm to about 0.65 mm in some implementations.

In some embodiments, spherical members may be formed directly on ends of the elongate members 111 using a precision laser weld technique (e.g., using an Nd:YAG laser). Such embodiments can eliminate a need for the receptacles 150 and allow the elongate members 111 to be engaged directly with the sockets 140 of the hub 119. For example, the spherical member at the end of the elongate member 111 may be press-fit or snap fitted into the semi-spherical pocket 144 of the hub 119. In some examples, spherical members may alternatively be fixedly and directly attached to ends of the elongate members 111 instead of being integrally formed with the elongate members 111. For any of the examples discussed herein that describe receptacles 150 and a spherical member 152 of the receptacle, the receptacle 150 may generally be omitted, and a spherical member formed or attached at the end of an elongate member 111 may replace the spherical member 152.

Figure 3B:
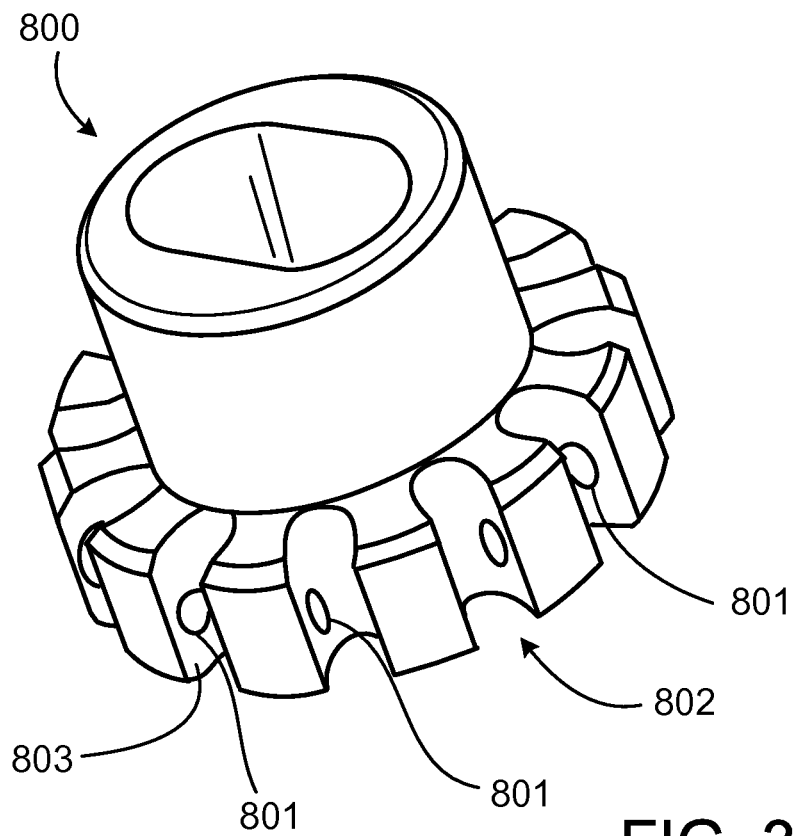
FIG. 3B is a perspective view of an alternative example hub that can be used with an occlusion device.

In some implementations, the semi-spherical pocket 144 described above can be replaced by two semi-spherical pockets that are disposed on opposing walls of a socket. FIG. 3B shows an alternative example hub 800 that includes twelve sockets 802 (though any appropriate number of sockets may alternatively be used). Opposing interior walls 803 of the sockets 802 each define a semi-spherical pocket 801. The semi-spherical pockets 801 can be machined into the interior walls 803 to form the semi-spherical pockets 801. The generally semi-spherical member 152 of the receptacle 150 may be snapped into the socket 802, for example, either by the geometry of the ball or by providing opposing protrusions extending from opposite sides of the ball. The semi-spherical member 152 may pivot in the semi-spherical pockets 801.

Referring again to FIG. 3A, as described above, the frame 110 of the occlusion device 100 in this example includes six elongate members 111 that each extend into a corresponding receptacle 150 (although only a single elongate member 111 and receptacle 150 are shown in FIG. 3A). The elongate members 111 may generally be conformable, fatigue resistant, and elastic such that the elongate members 111 have a stored length. The elongate members 111 may have a spring nature that allows them to collapse and elongate to a pre-formed shape (e.g., the frame 110 may have a pre-formed shape). In some implementations, the elongate members 111 can be collapsed for catheter-based or thoracoscopic delivery as the device assumes a delivery configuration, and can self-expand to an enlarged configuration, such as a deployed configuration (e.g., the configuration shown in FIG. 1) once positioned in a less restrictive environment, such as the cavity of the LAA.

In some embodiments, the elongate members 111 can include wires, such as spring wires, shape memory alloy wires, or super-elastic alloy wires. The elongate members 111 may be nitinol wires. In some embodiments, the diameter or thickness of the elongate members 111 may be about 0.20 mm to 0.40 mm, but in other embodiments elongate members 111 having smaller or larger diameters may be used. In some embodiments, each of the elongate members 111 has the same diameter. In some embodiments, one or more portions of the elongate members 111 may be tapered. The elongate members 111 may have a round cross-sectional shape or may have a cross-sectional shape that is not round, such as a rectangle or other polygon. Examples of other cross-sectional shapes that the elongate members 111 may have include a square, oval, rectangle, triangle, D-shape, trapezoid, or irregular cross-sectional shape formed by a braided construct. In some embodiments, an occlusion device may include flat elongate members 111. In some examples, the elongate members 111 may be formed using a centerless grind technique, such that the diameter of the elongate members 111 varies along the length of the elongate members 111.

In some embodiments, one or more projections (not shown) extend from a surface of the spherical members 152 and are sized to engage one or more detents positioned across a surface of the socket 140. In some examples, the detents on the sockets 140 and the projections extending from the spherical members 152 can allow the receptacles to be encouraged, biased, held, or locked in a particular position, such that the elongate members 111 can maintain a particular position to provide a desired shape to the frame 110. In some embodiments, each socket 140 includes one or more detents (not shown) sized to engage protrusions extending from receptacles positioned within the sockets 140.

In some embodiments, either or both of the one or more semi-spherical pockets 144 and the one or more semi-cylindrical channels 142 may include protruding lip features (not shown) that extend to opposing edges of the socket openings 146 and serve to constrain the neck regions 154 of the receptacles 150 as the receptacles 150 pivot within the sockets 140. In some embodiments, the sockets 140 may not include detents, but may instead include one or more alternative motion-limiting features, such as slots or openings sized to engage the protrusions extending from the receptacles.

Referring again to receptacle 150, neck region 154, which extends between spherical member 152 and tubular member 156, can be sized to allow the receptacle 150 to pivot within the socket 140. In some implementations, neck region 154 has a diameter that is less than the width of the socket opening 146. For example, neck region 154 may have a diameter of about 0.127 mm to about 0.25 mm less than that of the diameter of the spherical members 152. In some embodiments, the tubular member 156 may have an inner diameter of about 0.02 mm to about 0.05 mm larger than that of the thickness (e.g., diameter) of the elongate member 111, a wall thickness of about 0.07 mm to about 0.15 mm, and a length of about 1.0 mm to about 2.6 mm.

Figure 4:
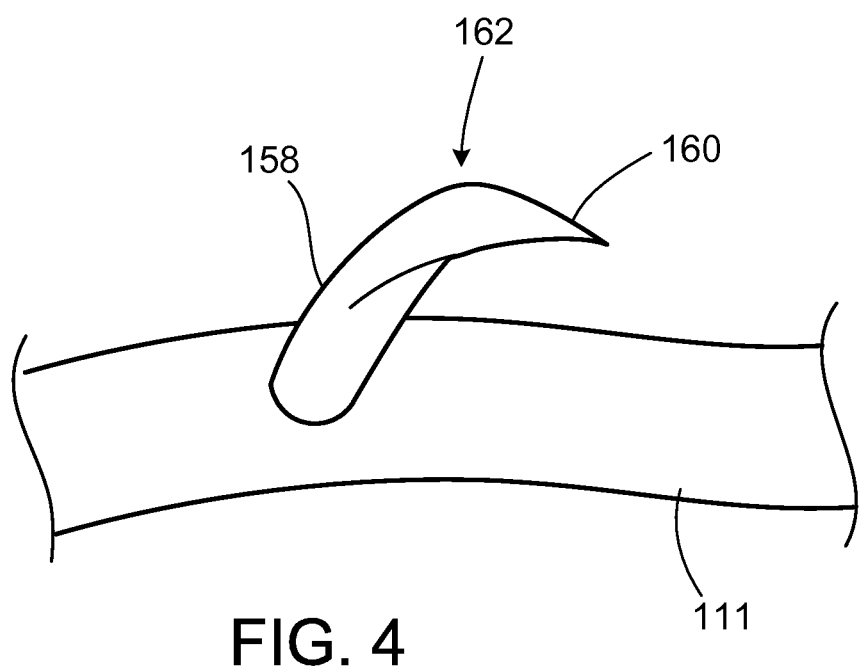
FIG. 4 is a perspective view of an example fixation member extending from an elongate member of the frame of FIG. 1.

Referring now to FIG. 4, a perspective view of a fixation member 158 extending from an elongate member 111 of the frame 110 of FIG. 1 is shown. Fixation members 158 can extend from surfaces of the elongate members 111 and can be formed to pierce tissue in a manner that secures the frame 110 at the delivery site. The fixation members 158 can be a biodegradable or bioabsorbable polymer or metal, for example, and thus may be resorbed over a period of time. In some examples, the bioabsorbable nature of the fixation members 158 may promote acute fixation of the occlusion device 100 at the delivery site, facilitate tissue ingrowth, and reduce the risk of undesired tissue perforation. The fixation members 158 may terminate at a sharp point 160. In various implementations, the fixation members 158 may be spaced from one another along the surface of the elongate members 111, for example about equidistant from one another along an outer rim of a distal portion of the support member 117. In some implementations, fixation members 158 may be spaced from one another based on a length of the elongate members 111, or on a portion of the elongate members 111, and a number of fixation members 158 included with the device. In some embodiments, the fixation members 158 include respective bends 162 along the lengths of the fixation members 158. In some examples, the bends 162 allow the fixation members 158 to collapse against the elongate members 111 while the occlusion device 100 is disposed within a catheter sheath. In some embodiments, the bend radii of the fixation members 158 may be about 1.5 mm to about 5.1 mm.

In some embodiments, the fixation members 158 may be compliant, non-compliant, or partially compliant and partially non-compliant. In some embodiments, a portion or the entire surface of the fixation members 158 may be coated with one or more biocompatible materials including a fluoropolymer (e.g., PTFE), a polyester, a silicone, a urethane, or another suitable biocompatible material. In some embodiments, coated portions of the fixation members 158 may provide a substrate that promotes tissue ingrowth around the fixation members 158. In some embodiments, the coated portions of the fixation members 158 substantially prevent tangling of fixation members 158 amongst each other. In some embodiments, the covered portions of the fixation members 158 minimize friction between the fixation members 158 and a surrounding catheter wall, thereby aiding deployment of the occlusion device 100 at a delivery site or retrieval of the occlusion device 100 from the delivery site following implantation. In some examples, the covered portion of the fixation members 158 may limit the extent to which the fixation members 158 can penetrate a tissue. In some embodiments, the covered portions of the fixation members 158 may be impregnated with or coated with one or more drug substances that are released in situ to promote wound healing or reduce tissue inflammation. In some embodiments, the drug substance may be a corticosteroid, a human growth factor, an anti-mitotic agent, an antithrombotic agent, an anti-inflammatory agent, an analgesic, an anti-infective agent, or dexamethasone sodium phosphate. In some embodiments, the covered portions of the fixation members 158 may provide texture that aids in securing the occlusion device 100 to the surrounding tissue.

In some embodiments, fixation members do not pierce tissue at the delivery site but instead secure the frame 110 to the delivery site using, for example, friction or pressure. In some embodiments the fixation members terminate with an atraumatic ending (e.g. a ball or a plate). In some embodiments, the surface of the atraumatic ending is textured to further increase the friction between the fixation member and the tissue at the delivery site.

The fixation members 158 may be attached to the elongate members 111 of the frame 110 in a variety of manners. For example, a fixation member 158 may be welded to an elongate member 111, as by laser welding or RF welding, or bonded to the elongate member 111 by an adhesive bond, an ultrasonic bond, or other bonding method. In some examples, combinations of the foregoing fixation member 158 attachment techniques may be used on a device.

Referring again to FIG. 1, the elongate members 111 terminate at the distal end 108 of the occlusion device 100 and form the eyelet 106. The eyelet 106 includes a central hole 164 sized to engage a catheter for delivery of the occlusion device 100 to the delivery site. In some embodiments, the central hole 164 may have an inner diameter of about 1.5 mm to about 3.1 mm. The central hole 164 of the eyelet 106 can generally be configured for use with commercially available pre-shaped, positionable, bendable, or steerable delivery sheaths and delivery catheters. For example, in some embodiments, the central hole 164 may be non-circular (e.g., ovular) to provide for directional keying of the occlusion device 100 with a delivery catheter. In some embodiments, the eyelet 106 may have a length of about 3.8 mm to about 5.1 mm. In some embodiments, the elongate members 111 extend from the eyelet 106 at an angle of about 45° to about 80° when the frame 110 is deployed to its prescribed enlarged shape.

Still referring to FIG. 1, the covering 112 may be a porous, elastic member that can stretch and collapse to accommodate extension and collapse, respectively, of the elongate members 111. The covering 112 may be sized to cover either or both of the support member 117 (as shown in FIG. 1) and the occlusion member 115 of the occlusion device 100. Pores of the covering 112 may be sized to substantially, or in some examples completely, prevent passage of blood, other bodily fluids, and emboli. In some embodiments, the covering 112 provides a scaffold that promotes tissue ingrowth within the covering 112 and endotheliazation of the covering 112 for durable occlusion of an aperture and anchoring of the occlusion device 100 to the tissue adjacent to the aperture. In some embodiments, the covering 112 is configured such that the inhibition of fluid passage through the covering 112 is immediate and does not rely on a thrombotic process. In some embodiments, the covering 112 can be modified by one or more chemical or physical processes that enhance certain physical properties of the covering 112. For example, a hydrophilic coating may be applied to the covering 112 to improve the wettability and echo translucency of the covering 112. In some embodiments, the covering 112 may be modified with chemical moieties that promote one or more of endothelial cell attachment, endothelial cell migration, endothelial cell proliferation, and resistance to thrombosis. In some embodiments, the covering 112 may be modified with covalently attached heparin or impregnated with one or more drug substances that are released in situ to promote wound healing or reduce tissue inflammation. In some embodiments, the drug may be a corticosteroid, a human growth factor, an anti-mitotic agent, an antithrombotic agent, or dexamethasone sodium phosphate.

The various components (e.g., the hub 102 or 119, the receptacle 150, the elongate members 111, and the covering 112) of the occlusion device 100 can be formed of one or more of a variety of biocompatible materials. In some embodiments, either or both of the hub 102 or 119 and the receptacles 150 may be injection molded from one or more materials including stainless steel, titanium, polyetheretherketone (PEEK), polyethermide (PEI), polycarbonate, polyamide, polytetrafluoroethylene (PTFE), NiTi, L605 (Cobalt Chromium), MP35N, or any other appropriate material. In some examples, the hub base members 114, 116 can be assembled with a press-fitting, a snap-fitting, an adhesive substance, or a weld (e.g., a laser weld) between the central hole 118 within the first hub base member 114 and the projection 120 extending from the second hub base member 116.

In some embodiments, the receptacles 150 may be formed of one or more materials including without limitation nitinol (NiTi), stainless steel, L605 alloy, MP35N alloy, and titanium. The elongate members 111 may generally be formed of one or more of any biocompatible materials that are sufficiently strong, conformable, and fatigue resistant. In some embodiments, the elongate members 111 may be formed as wires. In some embodiments, the elongate members 111 may be formed of NiTi, which has super-elastic properties that makes it a particularly good material from which to form such elongate members 111. For example, elongate members formed from NiTi can be heat set into a prescribed shape (e.g., in a manner such that the elongate members 111 provide the frame 110 with the shape shown in FIG. 1). In some embodiments, the elongate members 111 may be formed of a drawn-filled type of NiTi tubing that includes a different type of material at its core. For example, the core may include a radiopaque metal such as platinum. In some embodiments, the elongate members 111 may be formed of one or more materials including L605 steel, stainless steel, or any other biocompatible material that is suitably deformable.

In some examples, the eyelet 106 and frame 110 of the occlusion device 100 may be wound first, and the receptacles 150 and hub 102 or 119 attached thereafter. In some examples, the receptacles 150 may be attached to respective ends of the elongate members 111, the receptacles 150 may be attached to the hub 102 or 119, and then the elongate members 111 may be wound to form the frame 110 and the eyelet 106. In some examples, the receptacles 150 may be received by the hub assembly 102 or 119 prior to attaching the elongate members 111 to the receptacles 150, while in other examples the elongate members 111 may first be attached to the receptacles 150, and then the receptacles 150 may be received by the hub assembly 102 or 119.

In examples where spherical members are formed directly on the proximal ends of the elongate members 111, or attached thereto, the receptacles 150 may not be included with occlusion device 100, and the proximal ends of the elongate members 111 may be received directly within the sockets 140 of the hub 102 or 119. In some implementations, the eyelet 106 and the frame 110 may be wound first, and then the spherical members formed (or attached) at the proximal end of the elongate members 111 may be press-fit or snap-fitted into the sockets 140 of the hub 102 or 119. In some implementations, the spherical members formed (or attached) at the proximal end of the elongate members 111 may be press-fit or snap-fitted into the sockets 140 of the hub 102 or 119, and thereafter the frame 110 and eyelet 106 may be wound.

Some embodiments may comprise a covering 112. The covering 112, in some embodiments may be formed of a fluoropolymer (e.g., expanded PTFE (ePTFE) or PTFE). In some embodiments, the covering 112 may be formed of a polyester, a silicone, a urethane, or another biocompatible polymer, or combinations thereof. In certain embodiments, the covering 112 may be formed of a copolymer. In some examples, a first portion of the covering 112 may be formed of a first material and a second portion of the covering 112 may be formed of a second material. For example, the portion of the covering 112 that covers the occlusion member 115 may be formed of a first material, and the portion of the covering 112 that covers the support member 117 may be formed of a second material.

Figure 5:
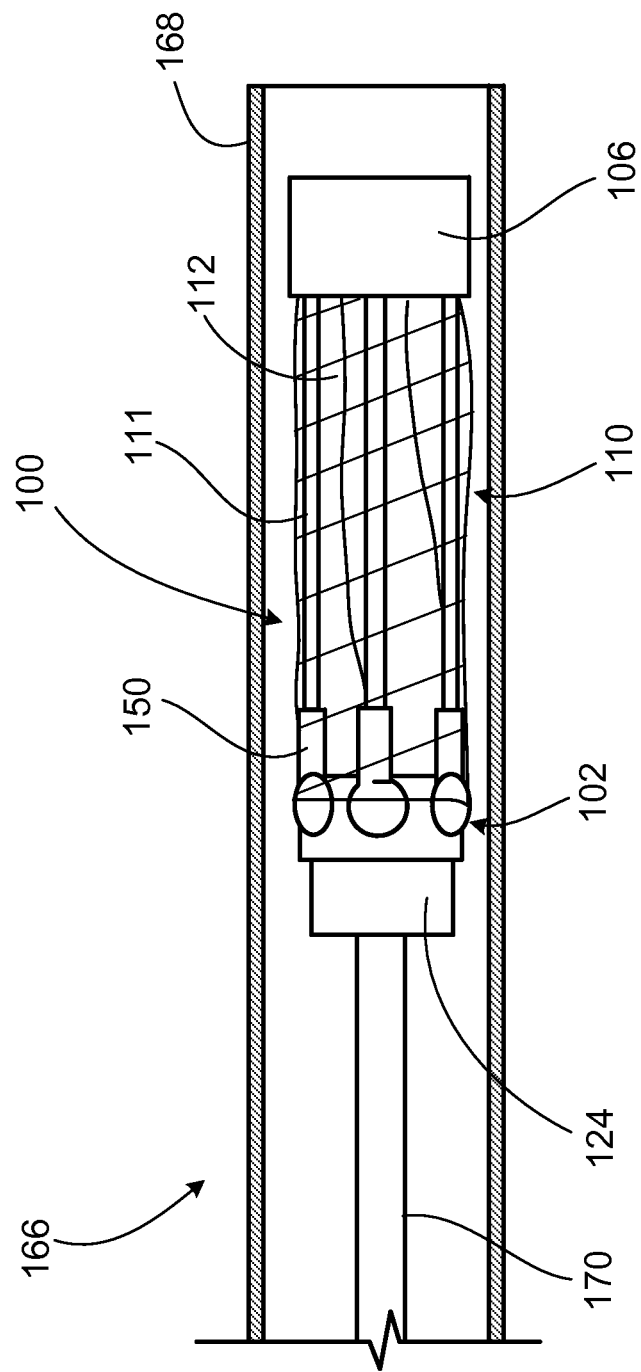
FIG. 5 is a side view of the occlusion device of FIG. 1 coupled with an example catheter delivery system.

Referring to FIG. 5, a side view of the occlusion device 100 of FIG. 1 coupled with a catheter delivery system 166 is shown. The occlusion device 100 can be delivered to a delivery site in an endovascular fashion using the catheter system 166. The catheter system 166 includes a delivery sheath 168 and a delivery catheter 170, a portion of which may be positioned generally concentrically within the delivery sheath 168. The occlusion device 100 can be loaded on the delivery catheter 170 by engaging a distal end of the delivery catheter with the hole 128 (see FIGS. 2 and 3A) defined by the tubular projection 124 of the hub 119. In some examples, an alternative delivery catheter may include an inner through-catheter component that passes through the hub of an occlusion device and that is attached to or engaged with the distal eyelet 106 of the occlusion device. In examples where a second hub 102 or 119 replaces the distal eyelet 106, the inner through-catheter component may attach to or be engaged with the second hub 102 or 119.

Coupled with the delivery catheter 170, the occlusion device 100 may then be forced through the delivery sheath 168 until the occlusion device 100 is positioned completely within the delivery sheath 168. As the occlusion device 100 is forced through the delivery sheath 168, the elongate members 111 of the frame 110 may collapse within the delivery sheath 168. For some implementations that include fixation members 158, the fixation members 158 may collapse against the elongate members 111 of the frame 110.

The configuration of device 100 shown in FIG. 5 may be referred to as the delivery configuration. As can be seen with reference to the delivery configuration of FIG. 5, the receptacles 150 and the attached elongate members 111 are pivoted about 90° (or more) as compared to their positions in the deployed configuration depicted in FIG. 1. This may permit a lower delivery profile, which may permit delivery of the occlusion device 100 using smaller catheters and/or sheaths. In this manner, navigating the occlusion device 100 may be easier within a tortuous vasculature, for example, potentially increasing patient comfort and safety, and shortening procedure duration. The lower delivery profile may also result in reduced frictional forces among the occlusion device 100, the catheter delivery system 166, and the delivery site. Such reduced frictional forces may accordingly reduce the amount of force required to deliver or retrieve the occlusion device 100, may potentially reduce abrasion that may occur between the occlusion device 100 and the various components of the catheter delivery system 166 (e.g., inner catheter surfaces) and may, therefore, reduce the amount and/or size of any particulates potentially generated. Such reduced risk of particulation may also permit the use of the use of smaller catheters and/or sheaths and may also reduce the amount of stress placed on one or more of the catheter components.

The occlusion device 100 and the catheter 170 may be advanced through the sheath 168 to the delivery site in a manner as would be known to one of ordinary skill in the art. At the delivery site, the occlusion device 100 may be deployed by pushing the delivery catheter 170 out of the delivery sheath 168 until the occlusion device 100 is positioned distal of the delivery sheath 168. As the occlusion device 100 moves distally out the delivery sheath 168, and as the frame 110 of the device 100 is liberated from the restrictive force imparted by the inner surface of the delivery sheath 168, the receptacles 150 (or an end portion of the elongate member 111 for embodiments that do not include receptacles 150) may pivot within the sockets 140 of the hub 102 to allow the frame 110 to expand to its prescribed shape. For implementations that include a detent feature, the receptacles 150 may pivot within the sockets 140 until the protrusions extending from the spherical members 152 of the receptacles 150 become substantially engaged with particular detents positioned along the semi-spherical pockets 144 of the sockets 140, thereby limiting further movement of the receptacles 150 within the sockets 140. For example, the detents may be engaged as the frame 110 conforms to its final shape at the delivery site. In some examples, the detents may be engaged in response to operator movement of a portion of the system that pushes the pivot hub into the almost fully formed frame shape. The forces generated by the engagement may be felt by the operator or may be observed using fluoroscopy or transesophageal echocardiography (TEE) imaging. In some examples where the sockets 140 do not include detents but instead include alternative motion-limiting features (e.g., a channel or slot), a cam-over effect or over-centering action may be utilized to limit a reverse movement or reverse pivot movement of the receptacles 150 or elongate member. In some embodiments, the cam-over effect or over-centering action may make the use of alternative motion-limiting features optional.

Figure 6:
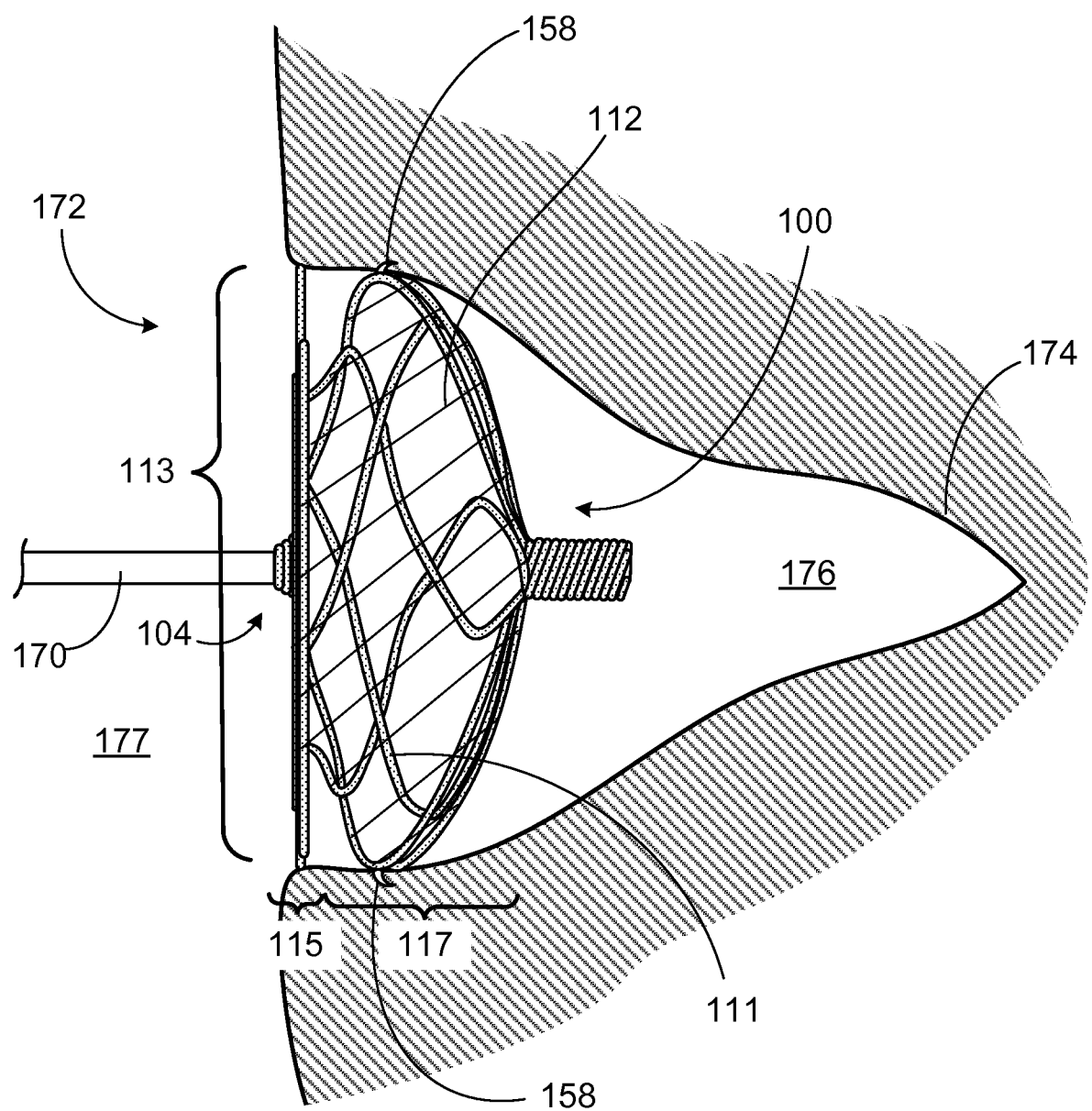
FIG. 6 is a side view of the occlusion device of FIG. 1, as implanted within a left atrial appendage.

Referring to FIG. 6, a side view of the occlusion device 100 of FIG. 1 deployed at a left atrial appendage delivery site is shown. The conformability of the elongate members 111 and the pivotal motion of the receptacles 150 (not shown in FIG. 6) within the sockets 140 allows the occlusion member 115 to be optimally positioned across the ostium 172 of the LAA 174, and the support member 117 to be optimally positioned within the cavity 176 of the LAA 174 such that the substantially planar face 113 effectively seals the LAA 174. One or more of the fixation members 158 may extend from the elongate members 111 to fixedly attach the device 100 to tissue of the LAA 174, which may restrict movement of the device 100 following deployment. The one or more fixation members 158 may impart a radial force on a tissue surface of the LAA 174. In some examples, the fixation members 158 may be disposed at portions of the frame that define an outer rim of the support member 117, as can be seen with respect to the two depicted fixation members 158 in FIG. 6. In some examples, fixation members 158 are omitted, and the elongate members 111 provide an apposition force against the wall of the LAA 174, which may secure the device 100 at the delivery site. The covering 112 may expand to accommodate the deployed frame 110.

Alternatively, the occlusion device 100 may be deployed by retracting the delivery sheath 168 while maintaining the position of the occlusion device 100 near the ostium 172 of the LAA 174. In some examples, the occlusion device 100 may be deployed by performing a combination of pushing the delivery catheter 170 out of the delivery sheath 168 and retracting the delivery sheath 168 while maintaining the position of the occlusion device 100. In some examples where the delivery catheter includes an inner through-catheter component, the delivery catheter may be attached to the occlusion device 100, to one or both of the proximal and distal eyelets, or to a hub. In some embodiments, one or more of the catheter components imparts an independent axial pistoning movement. In some embodiments, one or more catheter components impart an axial pistoning movement and one or more other catheter components serve an alignment function. In some embodiments, the delivery catheter is attached to the occlusion device 100 only at the proximal end of the occlusion device 100.

Still referring to FIG. 6 (and FIG. 1), deployed in its prescribed enlarged shape, a proximal portion of the frame 110 and the hub 102 may comprise the substantially planar face 113 so that no components of the frame 110 may protrude substantially beyond the proximal end 104 of the hub 102 into the left atrial chamber 177 at the proximal end 104 of the occlusion device 100. This may prevent or minimize a risk of blood flow disturbance and/or risk of thrombus formation or accumulation within the left atrial chamber 177 near the proximal end 104 of the occlusion device 100 compared to other devices that may include an eyelet at a left-atrial-facing end of the device, where the eyelet protrudes into the left atrium 177 or toward the left atrium 177. In some examples, flow models may be used to simulate blood flow fields resulting from particular configurations of the frame 110 and the hub 102. In some examples, color Doppler techniques and TEE imaging may be used to characterize blood flow patterns near the proximal end 104 of the occlusion device 100.

After the occlusion device 100 has been deployed within the LAA 174 at a desired position, the occlusion device 100 may be released from the delivery catheter 170, and the catheter delivery system 166 may be removed in an endovascular fashion, as is known to one of skill in the art. The occlusion device 100 may then be operable to substantially occlude the LAA 174.

In some examples, the occlusion device 100 can be repositioned within the LAA 174 (or other delivery site), or may be retrieved from the LAA 174 (or other delivery site) following implantation. For example, a retrieval cord can be included with a catheter delivery system. In some examples, the delivery catheter 170 can be used to reposition the occlusion device 100 while the occlusion device 100 is partially deployed by applying a gentle traction to the delivery catheter 170 until the occlusion device 100 collapses back within the sheath 168, or is positioned appropriately at the delivery site. In some examples, the retrieval cord can be coupled with the hub 102 and used to remove the deployed occlusion device 100 from the LAA 174 after the occlusion device 100 has been released from the delivery catheter 170 by pulling the entire occlusion device 100 out of the LAA 174 and back into the delivery sheath 168. In some examples, a retrieval cord can be engaged with a keyed hub. In other examples, the retrieval cord can be engaged with a threaded hub.

In some examples, the occlusion device 100 may alternatively be delivered to the LAA over a guidewire using rapid exchange or other methods of guidewire delivery known to those of ordinary skill in the art (see, for example, U.S. Pat. Nos. 5,040,548, 5,061,273, and 6,165,197 to Yock and U.S. Pat. No. 4,762,129 to Bonzel).

While the occlusion device 100 has been described as having the hub 102 positioned at the proximal end 104 of the occlusion device 100 and the eyelet 106 positioned at the distal end 108 of the occlusion device 100, in some embodiments, an occlusion device may have two hubs 102, one positioned at the proximal end 104 and the other at the distal end 108, and may omit the eyelet. In some examples, replacing the eyelet 106 at the distal end 108 of the occlusion device 100 with another hub 102 may provide a less traumatic interface between the distal end 108 of the occlusion device 100 and a wall of the LAA during initial deployment of the occlusion device 100 and following positioning of the occlusion device 100 within the LAA. Furthermore, providing a hub 102 at the distal end 108 of the occlusion device 100 may improve the conformability of the frame 110 to the cavity of the LAA. In some examples, implantable medical devices may include one, two, three, or more hub devices.

Figure 7:
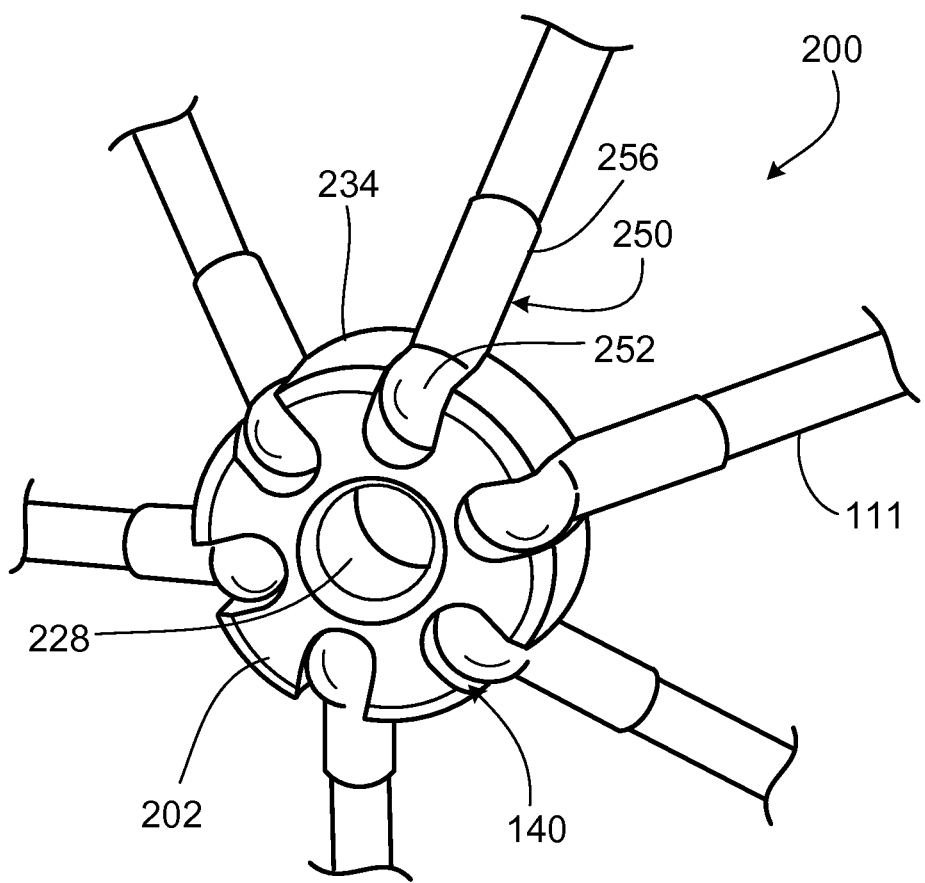
FIG. 7 is a perspective view of a portion of an occlusion device that includes an example one-piece hub member.

While the occlusion device 100 has been described as including the hub 102 formed of two hub base members 114, 116, in some embodiments, an occlusion device can alternatively include a hub that is formed of a single component. FIG. 7 is a perspective view of a portion of an occlusion device 200 that includes an example one-piece hub member 202. In some implementations, the hub 202 may be injection molded. The hub 202 is substantially similar in function to the hub 119 of FIGS. 2 and 3, and includes six sockets 140, each of which includes a socket opening defined by sidewall 234 of the hub 202. In this example, the sockets 140 are spaced substantially equidistantly around the hub 202.

Within each socket 140 is located a generally semi-spherical pocket (not shown in FIG. 7), defined by the hub 202, that constrains in a first dimension a generally spherical member 252 of a receptacle 250. The occlusion device 200 includes six receptacles 250, which function similarly to the receptacles 150 of FIGS. 2 and 3. The receptacles 250 include the generally spherical member 252, and a tubular member 256 that is attached to the generally spherical member 252. A first end of an elongate member 111 can be fixedly attached to a receptacle 250 at an attachment region. The receptacle 250 is configured to pivot with respect to the hub 202, such that the attachment region is movable with respect to the hub 202. The generally spherical members 252 may be snapped into the sockets 140, for example, and thereafter may pivot therein. As described above, a generally spherical member may alternatively be formed on an end of the elongate member 111, or attached thereto, and received within the sockets 140 (in such examples, the receptacle 250 may be omitted). The hub 202 defines a central through hole 228 that is sized to engage a distal end of a catheter (e.g., the delivery catheter 170). In some embodiments, the central through hole 228 may have a diameter of about 0.5 mm to about 1.5 mm.

Figure 8A:
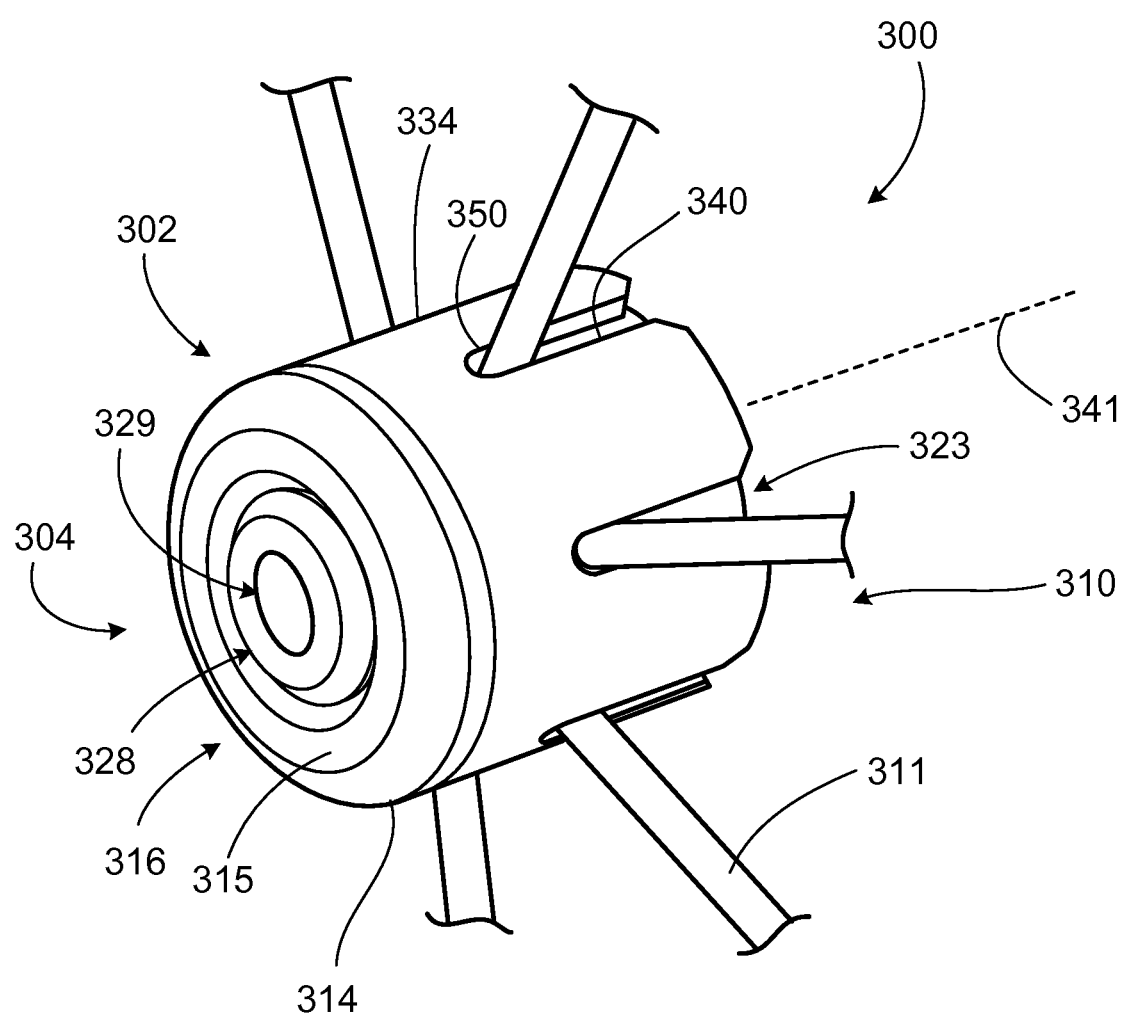
FIGS. 8A-8C are cutaway views of a portion of an example occlusion device that can be used to occlude apertures within a body of a patient.
Figure 8B:
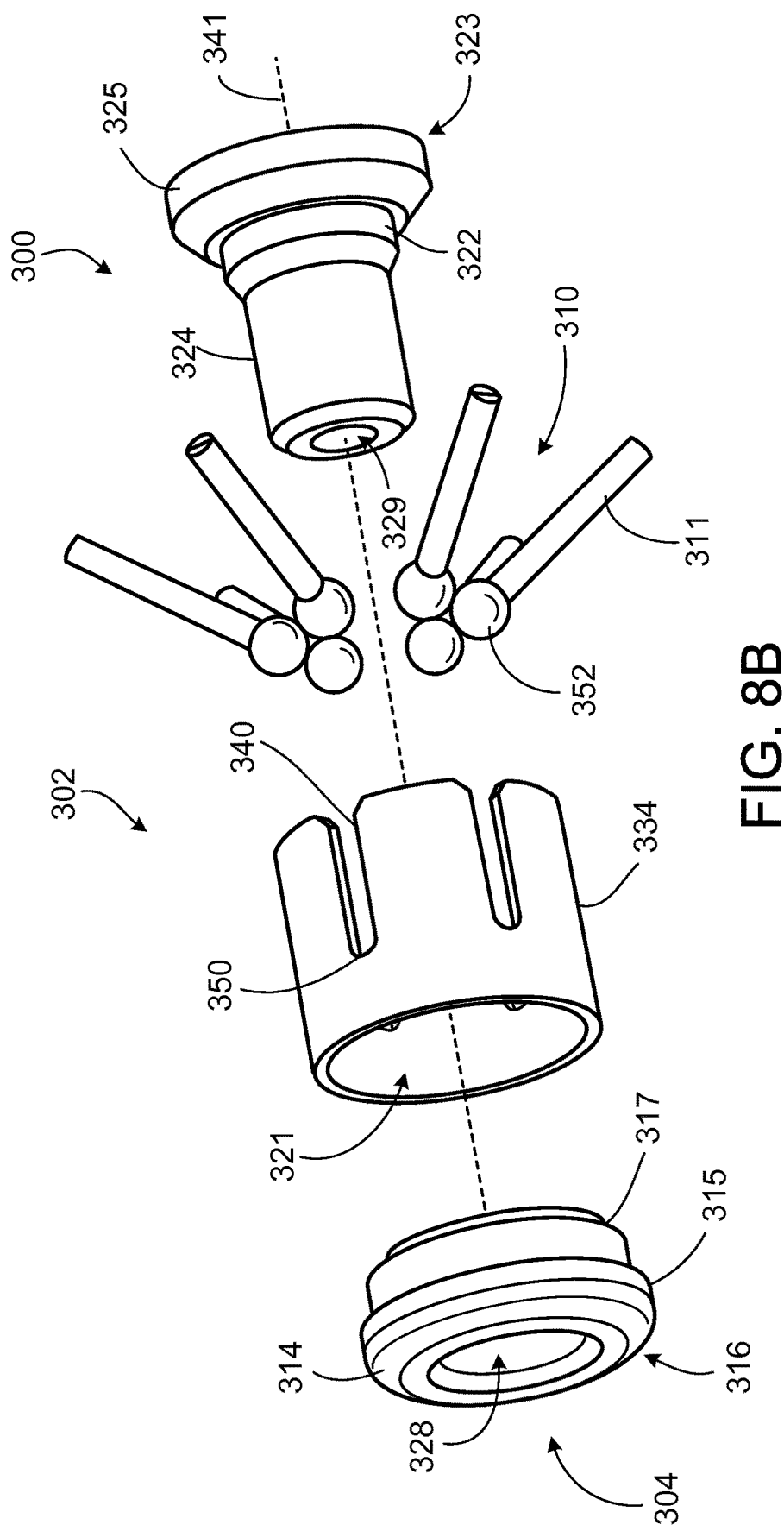
Figure 8C:
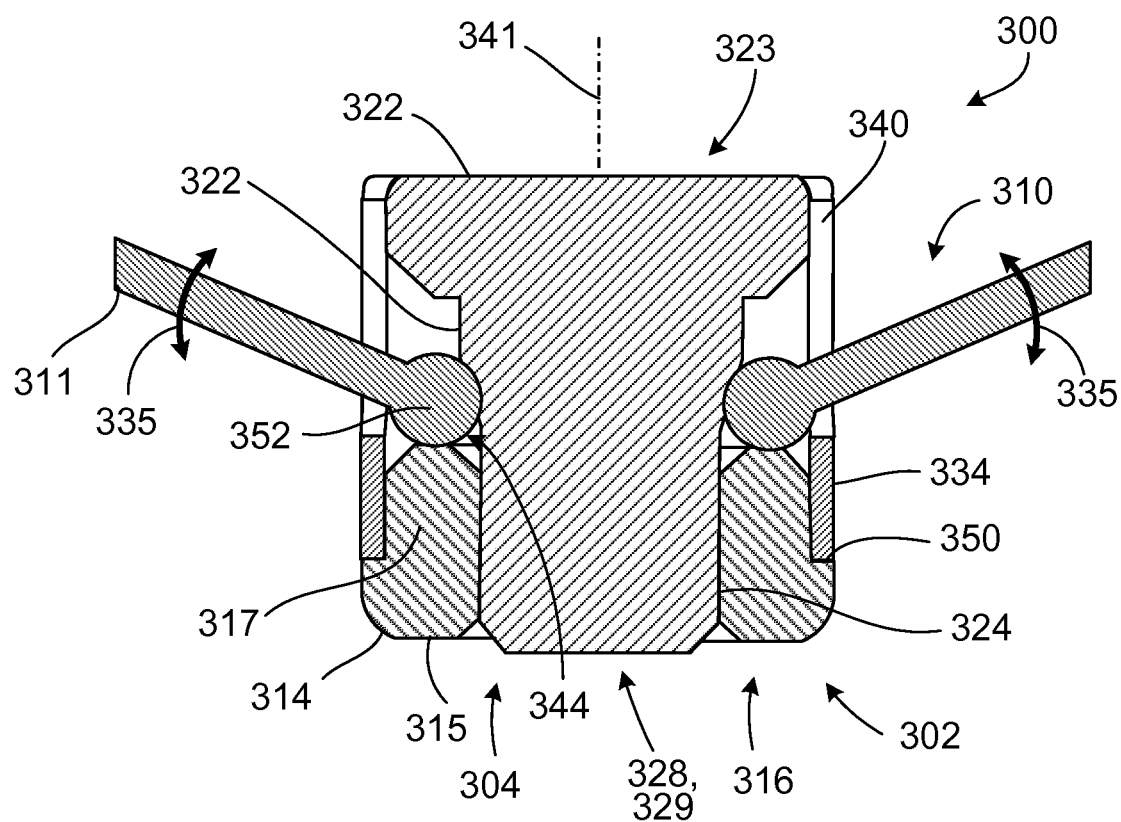

In some implementations, an occlusion device can include a hub assembly that guides the pivotal motion of elongate members. For example, a hub may include, for each elongate member, a slot that guides the pivotal motion of the elongate member. FIGS. 8A-8C show a proximal end 304 of an example occlusion device 300 that includes a hub 302 having six slots 340 formed in a tubular member 334 of the hub 302, and six respective elongate members 311 that have spherical members 352 (see FIGS. 8B and 8C) formed on ends of the elongate members 311. In some embodiments, the slots 340 may be substantially equally spaced around the tubular member 334 of the hub 302 and may, for example, be oriented parallel to a central axis 341 of the tubular member 334. The hub 302 further includes an end cap 316 and a support member 323 that engage the tubular member 334 to support the spherical members 352 formed on the ends the elongate members 311. In some embodiments, the elongate members 311 may terminate in receptacles (e.g., the receptacles 150) instead of having spherical members 352 extending from the ends of the elongate members 311. The end cap 316 includes a base 315, a lip 317 that extends from the base 315 and into a lumen 321 (see FIG. 8B) of the tubular member 334, and a through hole 328 that extends through the lip 317. The end cap 316 can provide axial alignment of the support member 323 with the tubular member 334 and may include features (not shown) that allow the hub 302 to be engaged with a delivery catheter, such as a spherical end, a threaded surface, or a quick-release mechanism. The end cap 316 may further provide features that minimize tissue trauma and minimize thrombus accumulation along the proximal end 304 of the hub 302, such as a rounded edge 314 along the base 315 of the end cap 316.

The support member 323 (see FIGS. 8B and 8C) is disposed within the lumen 321 of the tubular member 323 and includes a base 325, a transitional shaft 322 adjacent the base 325, and an elongate shaft 324 that extends from the transitional shaft 322 and through the hole 328 of the end cap 316. The support member 323 may include features (not shown) that allow the hub 302 to be engaged with a delivery catheter, such as a spherical end, a threaded surface, or a quick-release mechanism. For example, the elongate shaft 324 of the occlusion device 300 includes a central through-hole 329 that may be sized to engage a distal end of a delivery catheter (e.g., the delivery catheter 170). A configuration of the end cap 316 and the support member 323 provides an annular pocket region 344 (see FIG. 8C) that is formed from the lip 317 of the end cap 316 and from the transitional and elongate shafts 322, 324 of the support member 323. The spherical members 352 are received by the pocket regions 344, and the elongate members 311 extend through the respective slots 340 positioned along the tubular member 334. The pocket region 344 allows the spherical members 352 to pivot with one degree of freedom (as indicated by arrows 335 in FIG. 8C) within the lumen 321 of the tubular member 334, and the slots 340 guide positions of the elongate members 311 as the spherical members 352 pivot within the pockets 344. In some implementations, a thickness of the tubular member 334 may affect the degree to which the slots 340 guide the elongate members 311 as the spherical members 352 pivot within the pockets 344. In some embodiments, one or more of the lip 317 of the end cap 316 and the transitional and elongate shafts 322, 324 of the support member 323 may be formed to allow the spherical members 352 to pivot with more than one degree of freedom.

In some implementations, one or more of the slots 340, through which elongate members 311 extend, includes an edge 350 that may limit a proximal rotation of a portion of the elongate member 311 that passes through the slot 340. The slots 340 may have a width that allows passage of the elongate members 311 but that does not allow passage of the spherical members 352, and may thus limit constrain radial movement of the spherical members 352. The spherical members 352 may be retained within pocket regions 344. Referring particularly to FIG. 8C, an elongate member 311 may pivot inward towards the hub 302 until the elongate member 311 contacts the base 325 of the support member 323, which may prevent further movement in that direction.

The occlusion device 300 may generally include an occlusion member (e.g., an occlusion member similar to the occlusion member 115) and a support member (e.g., a support member similar to the support member 117). The elongate members 311 can extend from the slots 340 to form a substantially planar occluder face, can extend slightly proximal to the hub 302 to form a concave occluder face, or can extend slightly distal to the hub 302 to form a convex occluder face. In some embodiments, the slots 340 have a width of about 0.25 mm to about 0.31 mm and a length of about 0.75 mm to about 2.6 mm.

While in the depicted embodiments the portions of the elongate members 311 in proximity to the spherical members 352 is generally straight, in some embodiments, the elongate member 311 may include a bend in a portion of the elongate member proximate the spherical member 352. The bend may adjust an angle at which the elongate member 311 extends from the proximal end 304 of the occlusion device 300. In some embodiments, the elongate members 311 may be bent to an angle of about 10° to about 45° (e.g., 30°).

In some embodiments, the slots 340 may include an angle that biases the elongate members 111 in a desired direction relative to the tubular member 334 of the hub 302. In some embodiments, the spherical members 352 may have a diameter of up to two times that of the elongate members 311. The elongate members 311 may terminate at a distal end of the occlusion device 300 at an eyelet (e.g., the eyelet 106) or at another hub (e.g., the hub 102, 119, 202, or 302).

Figure 9:
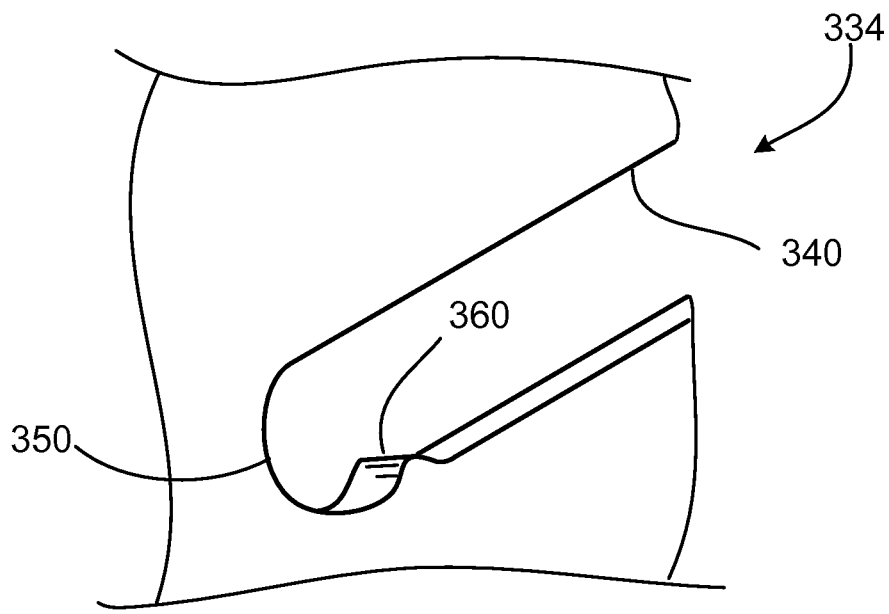
FIG. 9 is an enlarged cutaway view of an example tubular member of a hub of the occlusion device of FIGS. 8A-8C.

As shown in FIG. 9, in some embodiments, one or more slots 340 may include one or more detents 360. In this example, the detent 360 includes a ridge, over which the elongate member 311 (or spherical member 352 in some implementations) may pass as the elongate member 311 moves through the slot 340. In some examples, an additional force may be required to move the elongate member 311 beyond the ridge of the detent 360. In some examples, the detent 360 may maintain the spherical members 352 in a desired position. For example, the detent 360 shown in FIG. 9 may encourage or maintain the spherical member 352 or portion of the elongate member 311 near the edge 350 of the slot 340, in a longitudinal position near a proximal end of the slot 340. In various examples, one or more detents 360 may be located at various positions along the slots 340 to provide for various preferred positions of the spherical members 352, various locking forces, and various degrees of conformability of the frame 310.

In some embodiments, the detents 360 are positioned to maintain, once engaged, the spherical members 352 in a particular rotational position. In some embodiments, the detents are positioned to maintain, once engaged, the spherical members 352 in a particular longitudinal position. In some examples, the detents may allow the spherical members 352 to be maintained at about a 90° angle relative to the central axis 341 of the hub 302 when a frame 310 of the occlusion device 300 has assumed its deployed configuration (e.g., to form a substantially planar occluder face). In some examples, the detents 360 may allow the spherical members 352 to be maintained at an angle slightly greater than about 90° to achieve an inverted shape (e.g., to form a concave occluder face) for camming over the center. In some examples, the detents 360 may allow the spherical members 352 and the elongate members 311 to be generally collapsed along the slots 340 when the frame 310 is substantially collapsed (e.g., when the occlusion device 300 is in a delivery configuration). In some embodiments, a hub may include fewer than six slots 340 or more than six slots 340.

The various components of the occlusion device 300 may generally be formed of the same or similar materials as those discussed above with reference to the occlusion devices 100, 200. In some examples, the end cap 316 may be formed of one or more materials including stainless steel, L605, MP35N, PEEK, PTFE, or any other suitably hard, biocompatible plastic, for example. The various components of the occlusion device 300 may be assembled in a similar manner or in substantially the same manner as those of the occlusion devices 100, 200, with the exception of the hub 302. In some examples, the slots 340 may be laser cut into the tubular member 334 of the hub 302. A portion of the elongate members 311 adjacent the spherical members 352 may then be inserted within the respective slots 340 of the tubular member 334, and the lip 317 of the end cap 316 and the support member 323 may be snap-fitted into the lumen 321 of the hub 302.

Figure 10:
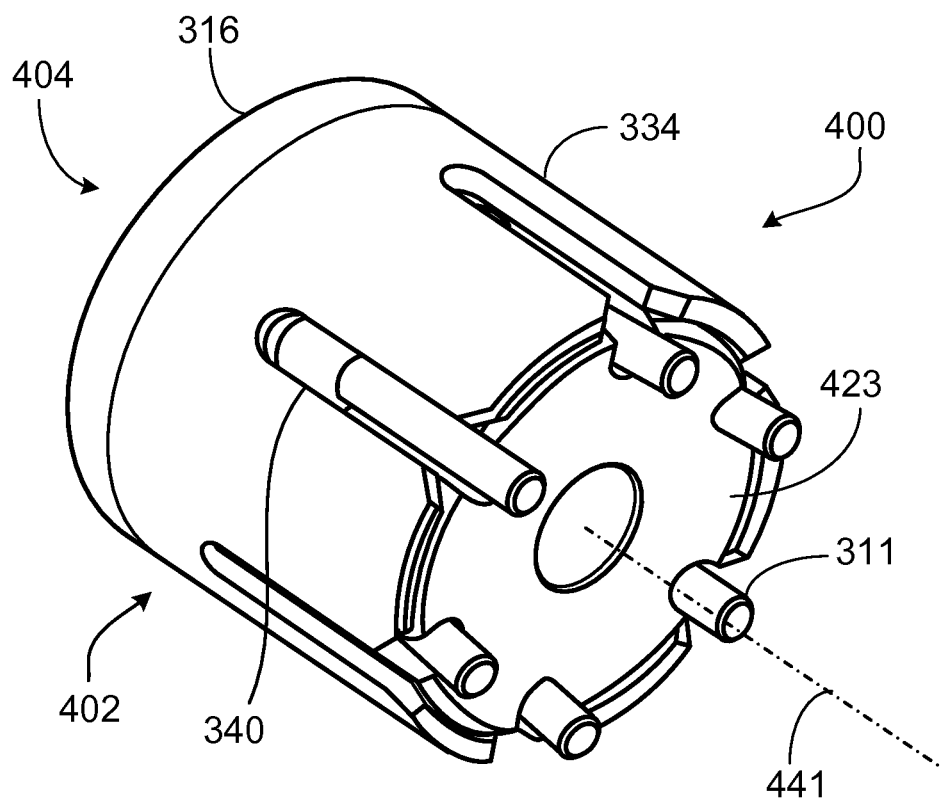
FIG. 10 is a cutaway view of a portion of an example occlusion device that can be used to occlude apertures within a body of a patient.

In some embodiments, an occlusion device may include a hub that allows elongate members to collapse substantially flush with an outer surface of the hub. For example, FIG. 10 shows a proximal end 404 of an occlusion device 400 that includes a hub 402 allowing the elongate members 311 to collapse parallel to a central longitudinal axis 441 of the hub 402 and substantially flush with a tubular member 334 of the hub 402. The various components of the occlusion device 400 may be substantially similar in construction to those of the occlusion device 300, with the exception of the hub 402. In some implementations, the hub 402 includes the end cap 316, the tubular member 334, and a support member 423.

Figure 11:
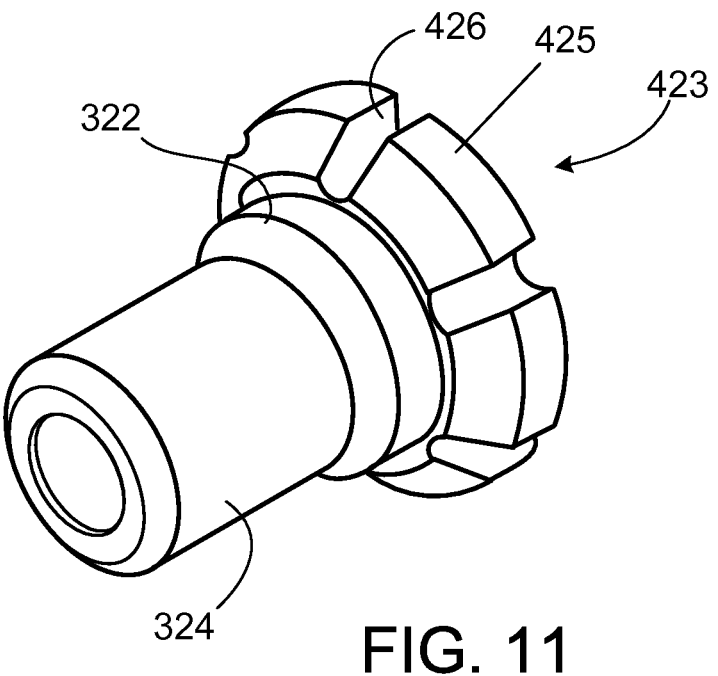
FIG. 11 is a perspective view of an example support member of a hub of the occlusion device of FIG. 10.

Referring now to FIG. 11, the support member 423 includes a base 425, the transitional shaft 322, and the elongate shaft 324. Six channels 426 extend from a sidewall of the base 425 and may be centrally aligned with the respective slots 340 of the tubular member 334 when the hub is assembled. The channels 426 may allow the elongate members 311 to collapse generally flush with the tubular member 334 and along the channels 426 (see FIG. 10), which can minimize a profile of the occlusion device 400 when the occlusion device 400 is in a delivery configuration and thereby improve the ease with which the occlusion device 400 may be inserted within a delivery sheath (e.g., the delivery sheath 168). The various components of the occlusion device 400 may generally be formed of the same or similar materials as those discussed above with reference to the occlusion devices 100, 200, and 300. The various components of the occlusion device 400 may be assembled in a similar manner or in substantially the same manner as that of the occlusion device 300.

Figure 12:
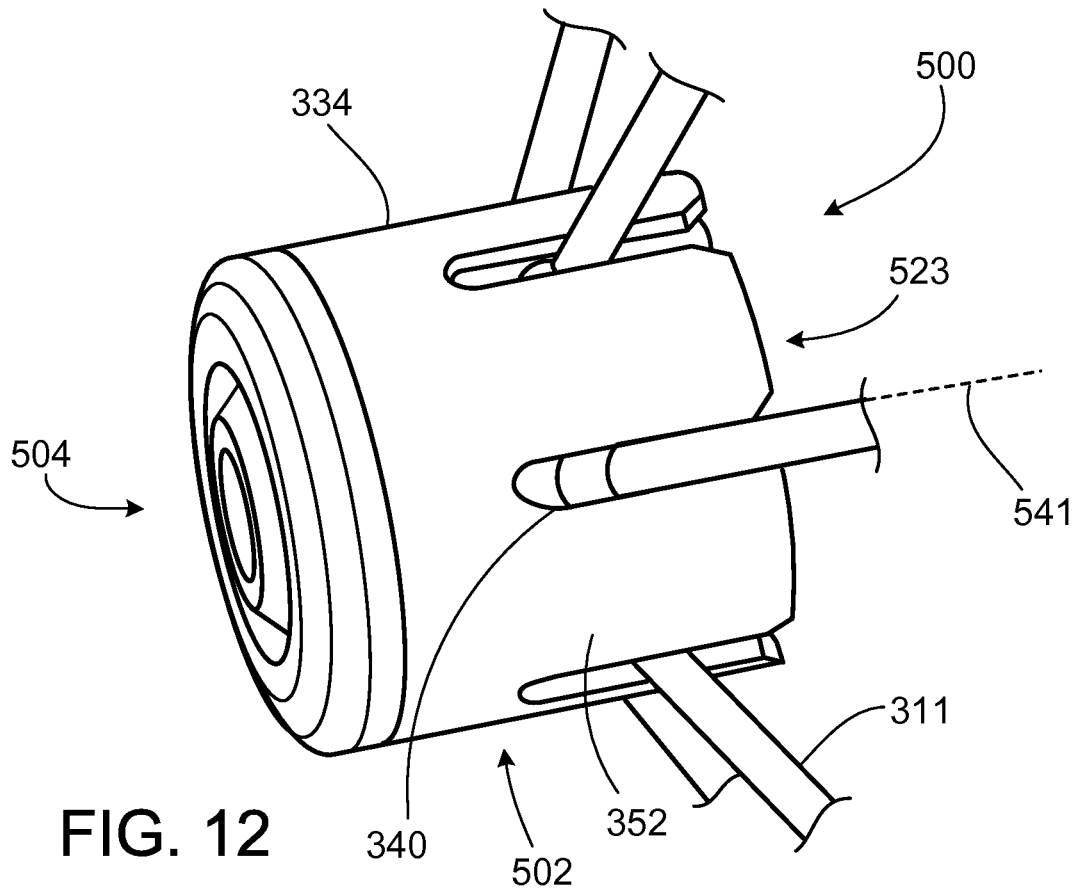
FIG. 12 is a cutaway view of a portion of an example occlusion device that can be used to occlude apertures within a body of a patient.

In some embodiments, an occlusion device may include a hub that allows elongate members to move with more than one degree of freedom (e.g., a first degree of freedom allowing a pivotal motion and a second degree of freedom allowing a translational motion). For example, FIG. 12 shows a proximal end 504 of an occlusion device 500 that includes a hub 502 allowing the elongate members 311 to translate in a direction parallel to a central axis 541 of the hub 502 and to collapse parallel to the central axis 541 and substantially flush with the tubular member 334 of the hub 502. The various components of the occlusion device 500 may be substantially similar in construction to those of the occlusion devices 300, 400, with the exception of the hub 502. The hub 502 includes the end cap 316, the tubular member 334, and a support member 523.

Figure 13:
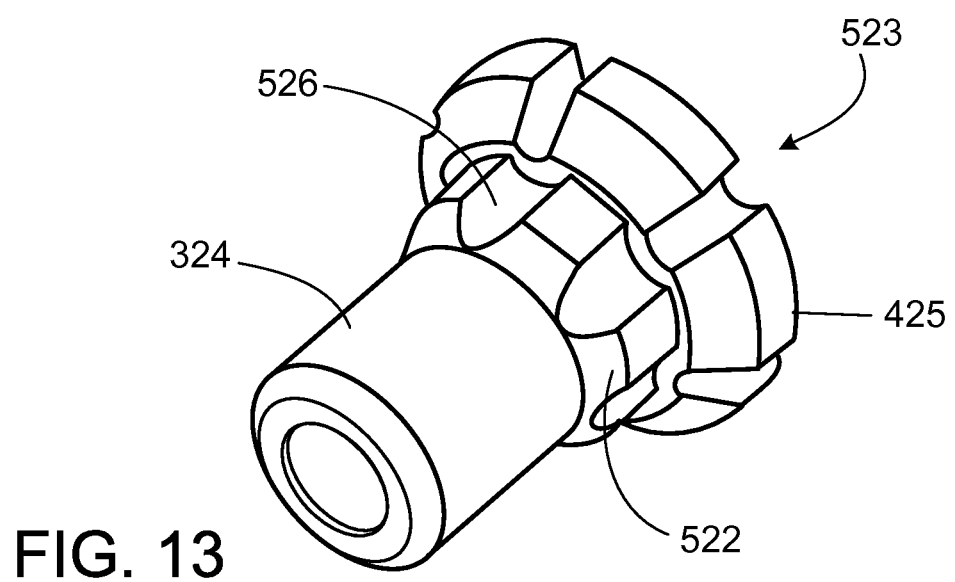
FIG. 13 is a perspective view of an example support member of a hub of the occlusion device of FIG. 12.

Referring to FIG. 13, the support member 523 includes the base 425, a transitional shaft 522, and the elongate shaft 324. Six channels 526 extend from a sidewall of the transitional shaft 522 and may be centrally aligned with the respective slots 340 of the tubular member 334 and the respective slots 426 of the base 425 when the hub is assembled. The channels 526 allow the spherical members 352 to translate out of the annular pocket region 344 (see FIG. 8C) and into the channels 526, which may provide the frame 310 with an increased degree of conformability. The slots 526 may extend through a portion or an entire length of the transitional shaft 522 to allow for varying degrees of translational motion of the spherical members 352 along the slots 340. In the example of FIG. 13, the channels 526 have a semi-cylindrical shape, but in some embodiments, such channels may have a different shape. The various components of the occlusion device 500 may generally be formed of the same or similar materials as those discussed above with reference to the occlusion devices 100, 200, 300, and 400. The various components of the occlusion device 500 may be assembled in a similar manner or in substantially the same manner as that of the occlusion devices 300, 400.

Figure 14:
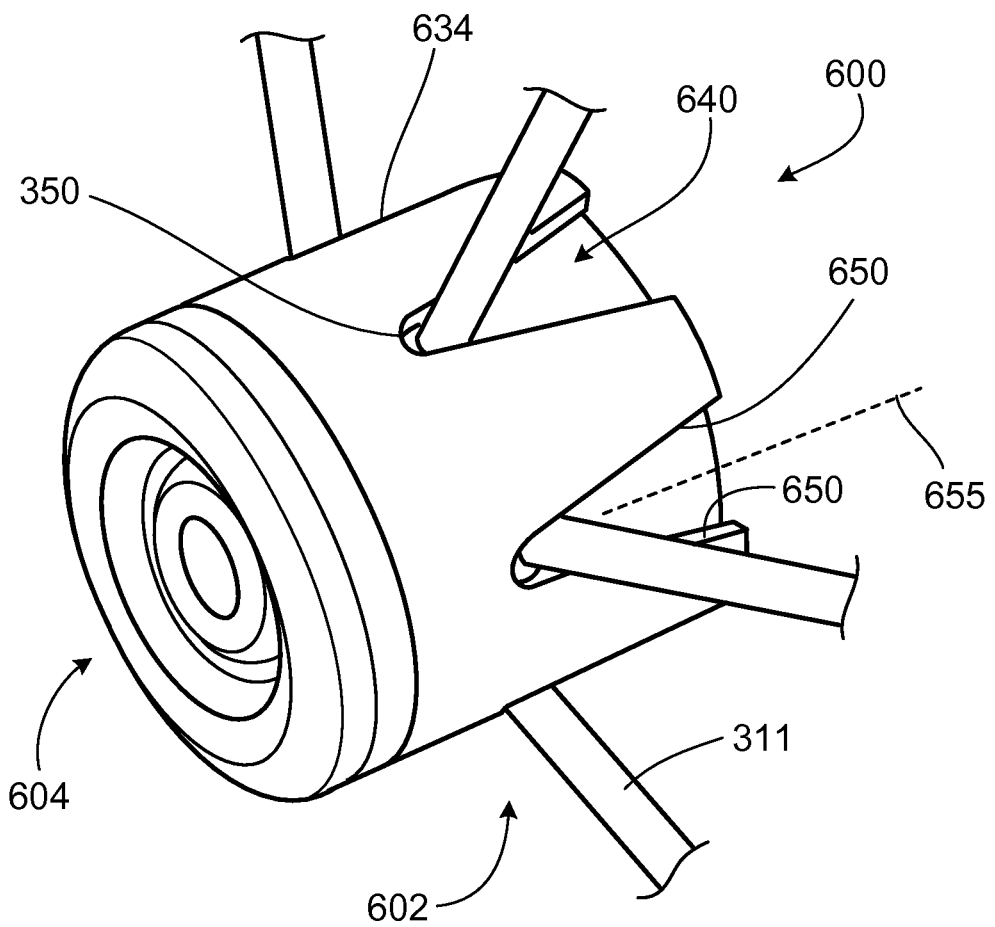
FIG. 14 is a cutaway view of a portion of an example occlusion device that can be used to occlude apertures within a body of a patient.

In some embodiments, an occlusion device may include a hub that allows elongate members to move with more than one degree of pivotal motion. For example, FIG. 14 shows a proximal end 604 of an occlusion device 600 that includes a hub 602 that allows the elongate members 311 to pivot laterally within slots 640 along a tubular member 634 in addition to the longitudinal pivotal motion allowed by the annular pocket region 344 (see FIG. 8C). The slots 640 include the edges 350 (of the slots 340) and opposing edges 650 and are positioned substantially equally around a circumference of the tubular member 634. The various components of the occlusion device 600 may be substantially similar in construction to those of the occlusion device 300, with the exception of the hub 602. The hub 602 includes the end cap 316, the tubular member 634, and the support member 323 (not shown). In some embodiments, the support member 323 may alternatively be replaced by the support member 423 or the support member 523.

In the depicted example, the opposing edges 650 of each slot 640 taper outward substantially equal distances from a central axis 655 of each slot 640, and allow for an increased degree of lateral movement of the elongate members 311 within the slots 640 as a distance from the edge 350 of the slot 640 increases. In this manner, in some examples a frame 310 of the occlusion device 600 may allow the occlusion device 600 to more easily collapse to a delivery configuration or to more easily conform to a geometry of the LAA.

The various components of the occlusion device 600 may generally be formed of the same or similar materials as those discussed above with reference to the occlusion devices 100, 200, 300, 400, and 500. The various components of the occlusion device 600 may be assembled in a substantially similar manner or in substantially the same manner as that of the occlusion devices 300, 400, and 500.

In some embodiments, an occlusion device may include a hub that has slots within a tubular member that has one edge that tapers with respect to a central axis of the slot and an opposing edge that may not taper with respect to the central axis of the slot (e.g., an opposing edge that is generally parallel to the central axis of the slot). In some examples, some or all slots positioned around the tubular member may have the same edge orientations. Such a slot configuration may allow positions of elongate members (e.g., the elongate members 311) to be biased towards one rotational direction (e.g., for embodiments of an occlusion device where the elongate members are right-handedly or left-handedly helically wound around an eyelet (e.g., the eyelet 106)). In some embodiments, slots having different edge orientations may be alternately positioned around the tubular member. Such a slot configuration may allow the elongate members to be alternately biased towards different rotational directions (e.g., for embodiments of an occlusion device where some elongate members are right-handedly helically wound around an eyelet (e.g., the eyelet 106)) and some elongate members are left-handedly helically wound around the eyelet.

Figure 15A:
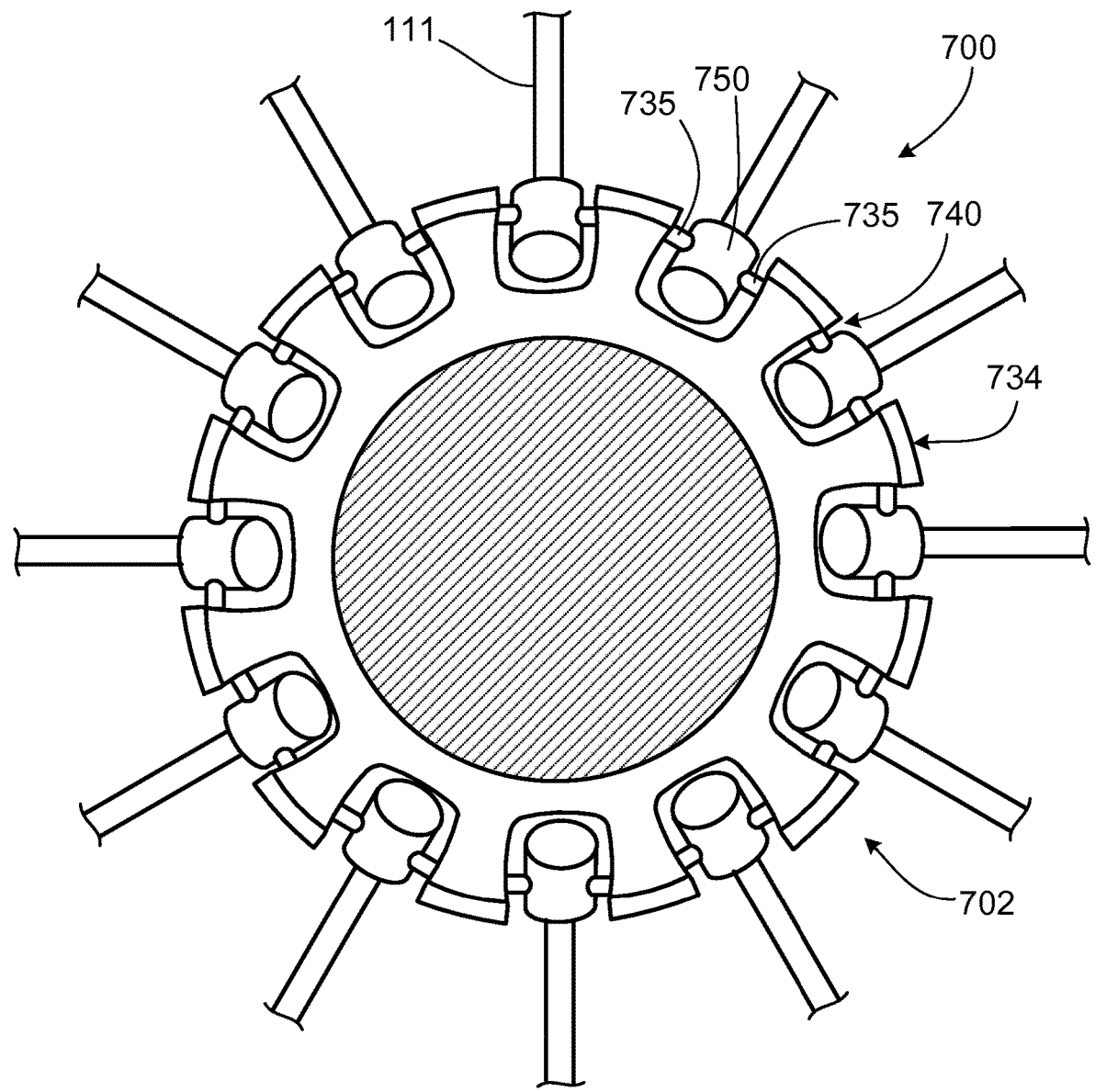
FIG. 15A is an end view of a portion of an example occlusion device that can be used to occlude apertures within a body of a patient.

In some embodiments, an occlusion device includes a hub having bucket-shaped receptacles attached to elongate members, where the bucket-shaped receptacles can pivot via attached pins that are also attached to the hub. For example, as shown in FIG. 15A, a portion of an example occlusion device 700 includes a hub 702 that has twelve bucket-shaped sockets 740 defined by a sidewall 734 of the hub 702. Interior of each socket 740 is disposed a bucket-shaped receptacle 750 that receives a corresponding elongate member 111 The elongate members 111 may be attached to the bucket-shaped receptacles 750 in manners similar to those described above with reference to elongate member attachment to receptacles 150. In other examples, an occlusion device may have more or less than twelve sockets and corresponding receptacles and elongate members (e.g., two, three, four, five, six, seven, eight, ten, fourteen, sixteen, etc.).

Figure 15B:
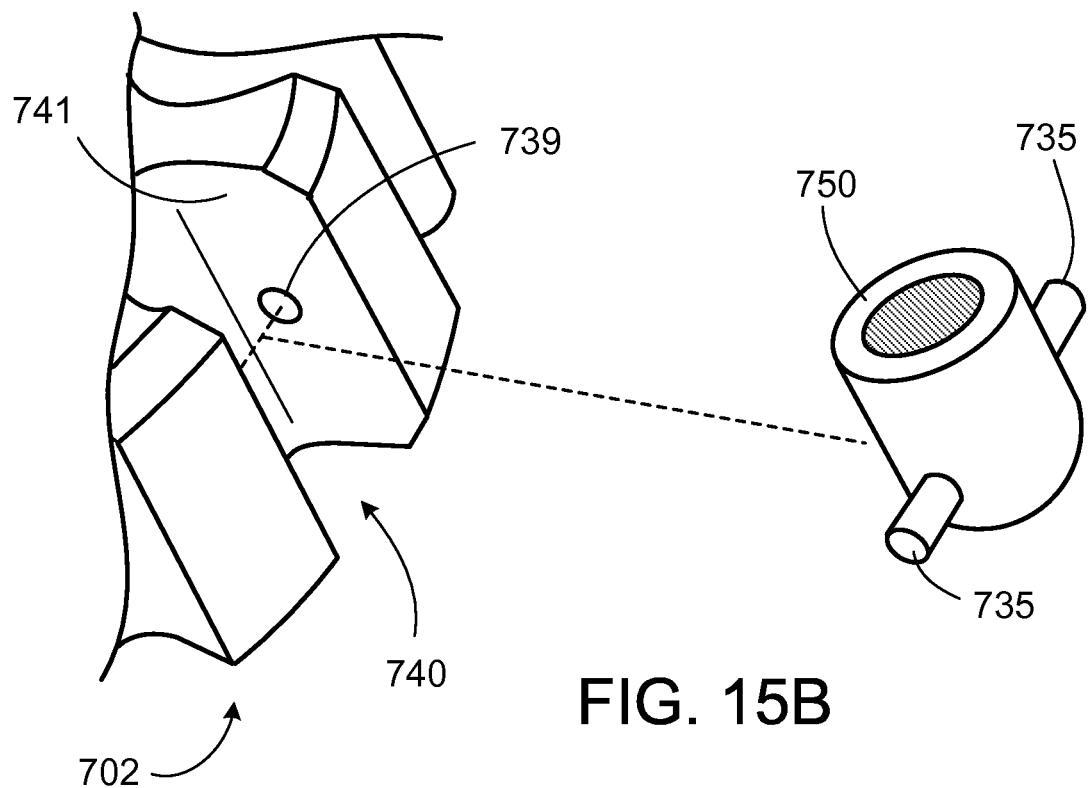
FIGS. 15B and 15C are perspective views that show example portions of the device of FIG. 15A.
Figure 15C:
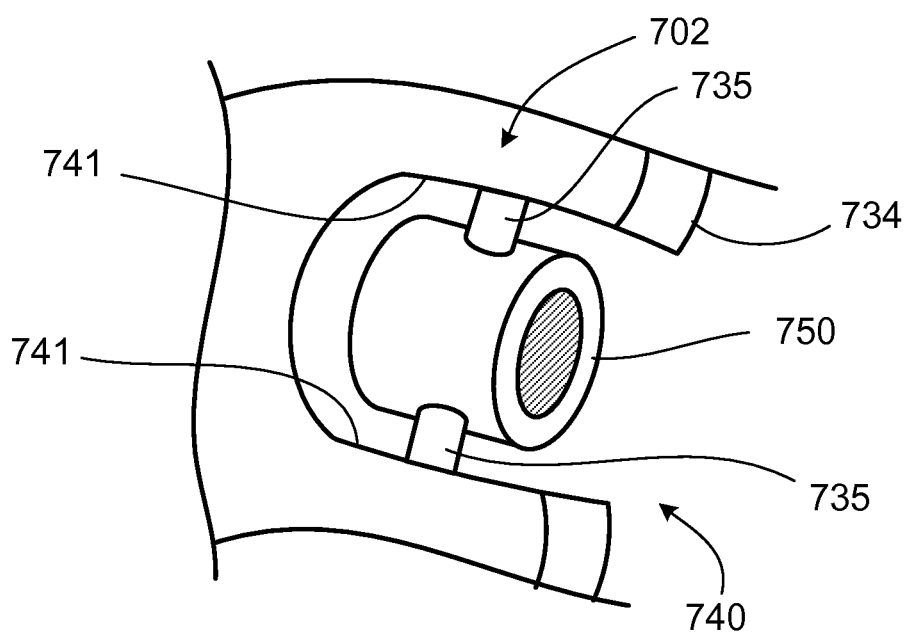

With reference to FIGS. 15B and 15C, in this example, each bucket receptacle 750 includes two pins 735 that are attached to and extend from the bucket receptacle 750. FIG. 15B shows a view of an isolated bucket receptacle 750 with pins 735 that extend from the receptacle 750. Also shown in FIG. 15B is a view of an isolated portion of the hub 702, showing a socket 740 without the bucket receptacle 750. Two holes 739, defined by opposing walls 741 of the socket 740, receive the pins 735 of the bucket receptacle 750. The receptacles 750 and the attached elongate members 111 can pivot on the pins 735. For example, the receptacles 750 and the attached elongate members 111 can pivot with one degree of freedom within the sockets 740 around an axis defined by the pins 735. FIG. 15C shows a portion of the hub 702, including one receptacle 750, and two pins 735 engaged with two holes 739 in the opposing walls 741 of the socket 740. In some implementations (not shown), the receptacles 750 may pivot on a single pin 735 which may be coupled to a wall 741 of the socket 740. The various components of the occlusion device 700 may be formed of the same or similar materials as those described above with reference to occlusion device 100.

While several of the hubs discussed herein have been described as including sockets or pockets that extend at an angle of about 90° from sidewalls of the hub (or from a plane tangential to a portion of the sidewalls near an elongate member entry point of the hub), in some embodiments, an occlusion device may include a hub that has sockets or pockets extending from sidewalls of the hub at an angle other than about 90° with respect to a horizontal reference axis of the sidewall. Without limitation, angles that sockets or pockets may extend from the sidewalls of a hub with respect to the horizontal reference axis of the sidewall can include about 80°, about 70°, about 60°, about 50°, about 40°, about 30°, about 20°, or about 10°. Accordingly, spherical members (e.g., the spherical members 152 of the receptacles 150 or the spherical members 352) may be positioned within the sockets or pockets at an angle that can allow elongate members (e.g., the elongate members 111, 311) of a frame to be arranged in a helically wound frame construct. In some examples, such a configuration of the sockets and the spherical members may be provided in an occlusion device that includes more than one hub on one end of the occlusion device. Some implementations of an occlusion device can include two or more hubs on one end of the occlusion device, where a first hub terminates elongate members that are wound in a first direction (e.g., in a leftward or counterclockwise direction), and a second hub terminates elongate members that are wound in a second direction (e.g., in a rightward or clockwise direction). Such a hub arrangement may provide for an equal number of first-direction-wound and second-direction-wound elongate members, for example.

Similarly, sockets or pockets can extend at various angles from sidewalls of the hub (or from a plane tangential to a portion of the sidewalls near the elongate member entry point to the hub), with respect to a vertical reference axis of the sidewall. Without limitation, angles that sockets or pockets may extend from the sidewalls of a hub with respect to the vertical reference axis of the sidewall can include about 80°, about 70°, about 60°, about 50°, about 40°, about 30°, about 20°, or about 10°. Such angles may be varied, for example, to provide devices or portions of devices with particular shapes formed by the elongate members. In some implementations, an entry angle of about 45° with respect to a vertical reference axis may provide an occlusion member 115 (see FIG. 1) having a convex profile.

While several of the hubs discussed herein have been described as allowing the spherical members or elongate members to pivot with respect to the sockets and the slots, or to translate longitudinally (with respect to a central longitudinal hub axis), in some embodiments, an occlusion device may include a hub that has sockets or slots that allow spherical members or elongate members to translate radially from a central axis of the hub within the sockets or slots. For example, the spherical member or elongate member may move toward or away from a central longitudinal axis of the hub, according to some implementations. In some implementations, such movement may be substantially perpendicular to the central longitudinal axis of the hub, and in some implementations a channel or socket may be configured to permit movement at other angles (e.g., about 120°, about 110°, about 100°, about 80°, about 70°, about 60°, or other appropriate angle). In some embodiments, such sockets or slots may have a width that varies in a direction that is radial to the central axis, such that the sockets or slot may bias spherical members to a preferred radial position. Such embodiments of an occlusion device may provide a frame of an occlusion device with an additional degree of conformability.

While some of the hubs discussed herein have been described as allowing the elongate members to pivot freely with one degree of freedom (as indicated, for example, by the arrow 153 in FIG. 3A), in some embodiments, an occlusion device may include a hub that allows elongate members to pivot from the hub with two or three degrees of freedom. For example, an occlusion device may include elongate members that are tethered to the hub in a manner that allows the elongate members to pivot in three dimensions (i.e., in any direction) with three degrees of freedom from an attachment point along the hub. In some examples, such a hub may be manufactured using an injection molding process that provides the attachment points as living hinges. In some embodiments, such an occlusion device may include elongate members (e.g., the elongate members 111) that terminate in receptacles (e.g., the receptacles 150) or elongate members (e.g., the elongate members 311) that have spherical members (e.g., the spherical members 352) on ends of the elongate members.

In another example, an occlusion device may include a hub that has a semi-spherical pocket extending from a sidewall of the hub (e.g., a donut-shaped hub) and respective elongate members (e.g., the elongate members 311) that have spherical members (e.g., spherical members similar to the spherical members 352) on ends of the elongate members such that the spherical members may be tethered to the semi-spherical pockets. In some examples, the spherical members may be tethered to the semi-spherical pockets with a tethering member such as a suture, another string-like member, or other flexible elongate member. In some embodiments, the tethering members may extend through the hub or be wrapped around the spherical members. Such a configuration of the spherical members being tethered to the hub may allow the elongate members to pivot in all directions (i.e., with three degrees of freedom) from the semi-spherical pockets.

While the occlusion devices 100, 200, 300, 400, 500, 600, 700, 800 have been described with respect to an LAA, in some embodiments, the occlusion devices 100, 200, 300, 400, 500, 600, 700, 800 can be used to occlude or seal other apertures within a body of a patient, such as a right atrial appendage, a fistula, a patent ductus arteriousus, a septal defect, a paravalvular leak, an arteriovenous malformation, or a body vessel.

The examples discussed herein have focused on occlusion devices, but it is contemplated that the hub assemblies described herein may also be used with other types of medical devices including both implantable devices and accessories. Examples of implantable devices and accessories include, without limitation, occlusion and closure devices, filters (e.g. inferior vena cava filter or an embolic protection filter), catheter based grabbers or retrieval devices, temporary filtration devices, and vessel sizers.

For additional examples of delivery system devices, systems, and techniques that can be used to deliver, deploy, reposition, and retrieve the devices discussed herein, see the provisional application titled "Implantable Medical Device Deployment System," having inventors Steven J. Masters and Thomas R. McDaniel, filed on 16 Nov. 2012, assigned U.S. Ser. No. 61/727,328 and non-provisional patent application titled "Implantable Medical Device Deployment System," having inventors Steven J. Masters and Thomas R. McDaniel, filed on 15 Mar. 2013, the disclosures of which are considered part of and are specifically incorporated by reference in their entirety (including the figures) for all purposes in the present disclosure.

For additional examples of medical devices that can use the hub features described herein, see the provisional patent application titled "Space Filling Devices," having inventors Coby C. Larsen, Brandon A. Lurie, Steven J. Masters, Thomas R. McDaniel, and Stanislaw L. Zukowski, filed on 16 Nov. 2012, assigned U.S. Ser. No. 61/727,458 and the provisional patent application titled "Space Filling Devices," having inventors Coby C. Larsen, Brandon A. Lurie, Steven J. Masters, Thomas R. McDaniel, and Stanislaw L. Zukowski, filed on 15 Mar. 2013, the disclosures of which are considered part of and are specifically incorporated by reference in their entirety (including the figures) for all purposes in the present disclosure.

Several characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shapes, sizes, and arrangements of parts including combinations within the principles described herein, to the full extent indicated by the broad, general meaning of the terms in which the appended claims are expressed. To the extent that these various modifications depart from the spirit and scope of the appended claims, they are intended to be encompassed therein. All references, publications, and patents referred to herein, including the figures and drawings included therewith, are incorporated by reference in their entirety.

What is claimed is:

1. A device for occluding an aperture in a body of a patient, comprising:
  a frame comprising a plurality of elongate members, and
  a hub component comprising a first base member and a second base member configured to engage together; and
  a plurality of attachment members arranged circumferentially and spaced substantially equidistantly about the hub component, the hub component being formed by a plurality of sockets when the first base member and the second base member are engaged, and a first end of each elongate member is fixedly attached to an attachment member of the plurality of attachment members at an attachment region, and a number of the plurality of elongate members is equal to a number of the plurality of attachment members;
  wherein the frame and the hub component together form at least one occlusive element, and wherein a proximal portion of the frame comprises a substantially planar face and the hub does not protrude substantially beyond the proximal portion of the frame with the plurality of elongate members extending from the substantially planar face and the plurality of elongate members each form a curvature tapering the frame to a distal end portion of the frame to reduce a diameter of the frame ending the curvature at the distal end portion and the frame includes one or more fixation members spaced from one another along an outer rim of the frame at the curvature of the plurality of elongate members, and wherein each attachment member of the plurality of attachment members is configured to pivot with respect to the hub component, such that each of the attachment members is movable with respect to the hub component.

2. A device according to claim 1, further comprising a covering that covers at least a portion of the frame.

3. A device according to claim 2, wherein the covering comprises a membrane.

4. A device according to claim 3, wherein the membrane comprises a fluoropolymer.

5. A device according to claim 4, wherein the membrane comprises one or more of expanded polytetrafluoroethylene (ePTFE) and polytetrafluoroethylene (PTFE).

6. A device according to claim 2, wherein the covering covers at least a portion of the hub component.

7. A device according to claim 3, wherein the membrane comprises a copolymer.

8. A device according to claim 1, wherein each attachment member of the plurality of attachment members comprises a generally spherical member, each of the generally spherical members being received by a socket of the plurality of sockets to form a ball-and-socket arrangement.

9. A device according to claim 8, wherein each socket of the plurality of sockets comprises one or more positional stops adapted to maintain a position of the received generally spherical member.

10. A device according to claim 8, wherein a tension on each of the generally spherical members increases as each of the generally spherical members pivots within a respective socket of the plurality of sockets.

11. A device according to claim 1, wherein each attachment member is movable with multiple degrees of freedom with respect to the hub component and the first hub base member includes a central hole that is sized to receive a central, elongate projection that extends from a distal surface of the second hub base member.

12. A device according to claim 1, wherein each attachment member is movable with one degree of freedom with respect to the hub component.

13. A device according to claim 1, wherein each elongate member of the plurality of elongate members is formed from a single wire.

14. A device according to claim 1, wherein the hub component is disposed at a proximal end of the device, and wherein the device further comprises an eyelet disposed at the distal end portion of the device.

15. A device according to claim 1, wherein the plurality of attachment members are substantially equally spaced about the hub component.

16. A device according to claim 1, wherein the hub component is disposed substantially at a center of the at least one occlusive element.

17. A device according to claim 1, wherein each elongate member of the plurality of elongate members moves, at the respective attachment member, independently of other elongate members of the plurality of elongate members.

18. A device according to claim 1, wherein the plurality of elongate members have an elastic property and a preformed shape, and wherein the frame can collapse to assume a delivery configuration and can expand to the preformed shape to assume a deployed configuration.

19. A device according to claim 1, wherein at least one elongate member of the plurality of elongate members moves parallel to a center axis of the hub component.

20. A device according to claim 1, wherein the hub component defines an aperture disposed along a center axis of the hub component, the aperture passing through the hub component.

21. The device according to claim 1, wherein the plurality of attachment members comprise receptacles.

22. The device according to claim 1, wherein the plurality of attachment members are integral with the first end of the plurality of elongate members.

* * * * *